United States Patent
Hershkovich

(10) Patent No.: US 12,282,309 B2
(45) Date of Patent: Apr. 22, 2025

(54) METHODS, SYSTEMS, AND APPARATUSES FOR GUIDING TRANSDUCER ARRAY PLACEMENT

(71) Applicant: Novocure GmbH, Root D4 (CH)

(72) Inventor: Hadas Sara Hershkovich, Haifa (IL)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 17/642,053

(22) PCT Filed: Oct. 7, 2020

(86) PCT No.: PCT/IB2020/000821
§ 371 (c)(1),
(2) Date: Mar. 10, 2022

(87) PCT Pub. No.: WO2021/069966
PCT Pub. Date: Apr. 15, 2021

(65) Prior Publication Data
US 2024/0061398 A1    Feb. 22, 2024

Related U.S. Application Data

(60) Provisional application No. 62/911,831, filed on Oct. 7, 2019.

(51) Int. Cl.
G05B 19/4099    (2006.01)
A61N 1/04    (2006.01)
A61N 1/40    (2006.01)
B33Y 50/00    (2015.01)
G06T 17/00    (2006.01)

(52) U.S. Cl.
CPC ....... *G05B 19/4099* (2013.01); *A61N 1/0484* (2013.01); *A61N 1/40* (2013.01); *B33Y 50/00* (2014.12); *G06T 17/00* (2013.01); *G05B 2219/49023* (2013.01); *G06T 2210/41* (2013.01)

(58) Field of Classification Search
CPC .... A61N 1/0484; A61N 1/40; A61N 1/36002; B33Y 50/00; G06T 17/00; G06T 2210/41; G05B 2219/49023; G16H 50/50
See application file for complete search history.

(56) References Cited

U.S. PATENT DOCUMENTS

| | | | |
|---|---|---|---|
| 7,565,205 B2 | 7/2009 | Palti | |
| 2002/0123679 A1 | 9/2002 | Dominguez | |
| 2004/0068296 A1* | 4/2004 | Palti | A61N 1/18 607/2 |
| 2016/0093100 A1* | 3/2016 | Ju | G05B 19/4099 700/98 |

(Continued)

FOREIGN PATENT DOCUMENTS

CN    107281635 A    10/2017

OTHER PUBLICATIONS

Joshua J. Timmons et al., "End-to-end workflow for finite element analysis of tumor treating fields in glioblastomas," Phys. Med. Biol., 62, 8264-8282.

(Continued)

*Primary Examiner* — Zhipeng Wang
(74) *Attorney, Agent, or Firm* — McCarter & English, LLP; Michael A. Sartori

(57) ABSTRACT

Methods, systems, and apparatuses are described for guiding placement of transducer arrays on a patient.

20 Claims, 16 Drawing Sheets

(56) References Cited

U.S. PATENT DOCUMENTS

| | | | |
|---|---|---|---|
| 2017/0120041 A1* | 5/2017 | Wenger | A61B 5/24 |
| 2018/0160933 A1* | 6/2018 | Urman | A61N 1/40 |
| 2020/0146586 A1* | 5/2020 | Naveh | A61B 6/501 |
| 2020/0219261 A1* | 7/2020 | Shamir | G06T 17/00 |

OTHER PUBLICATIONS

Zeev Bomzon et al., "Using Computational Phantoms to Improve Delivery of Tumor Treating Fields (TTFields) to Patient," IEEE, 6461-6464.

PCT International Search Report and Written Opinion issued in PCT/IB2020/000821, dated Mar. 26, 2021.

* cited by examiner

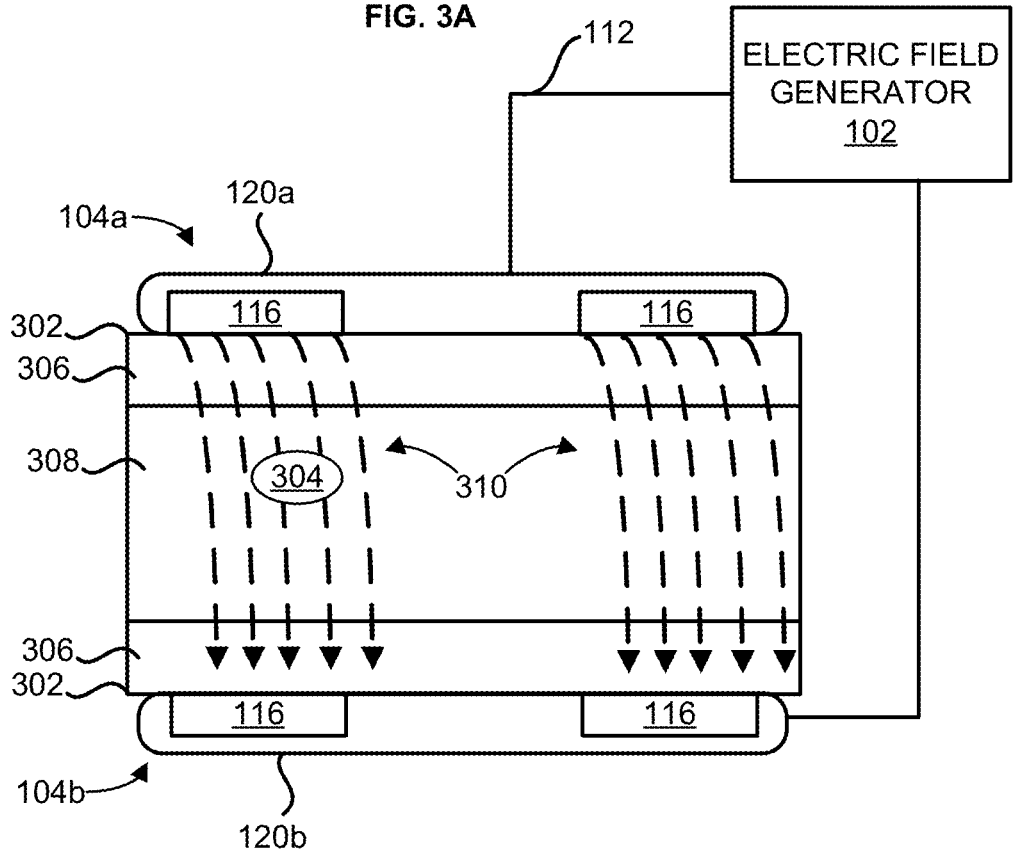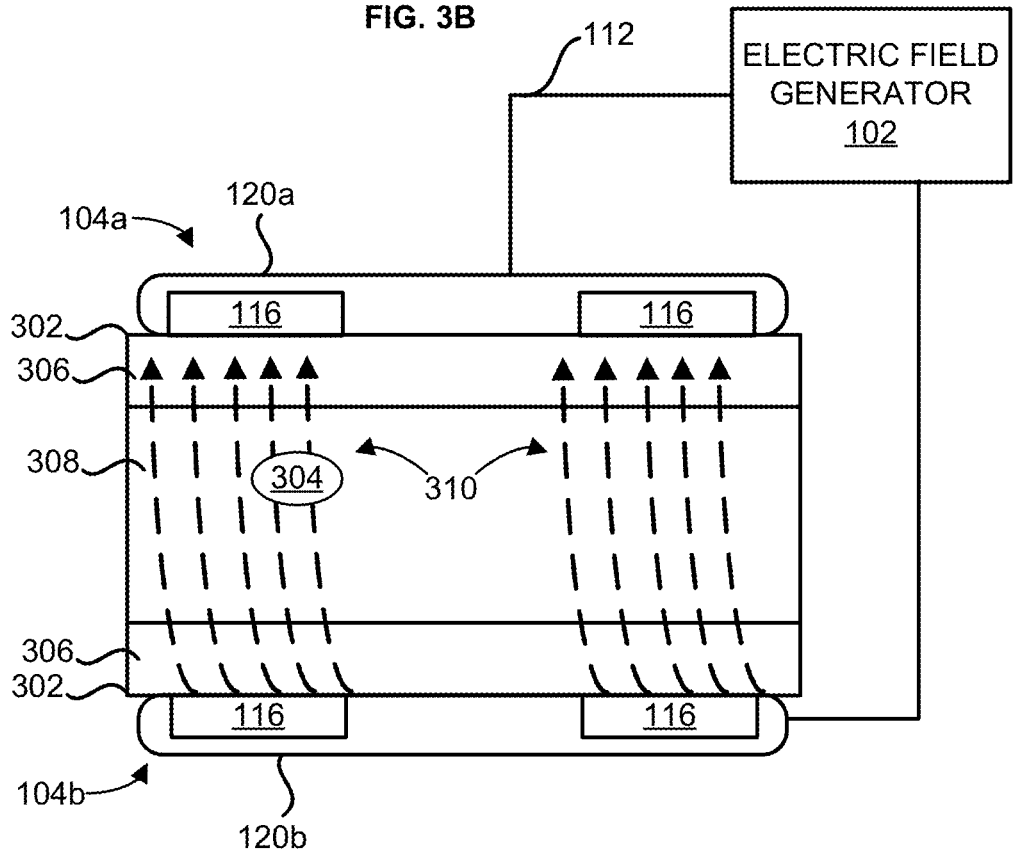

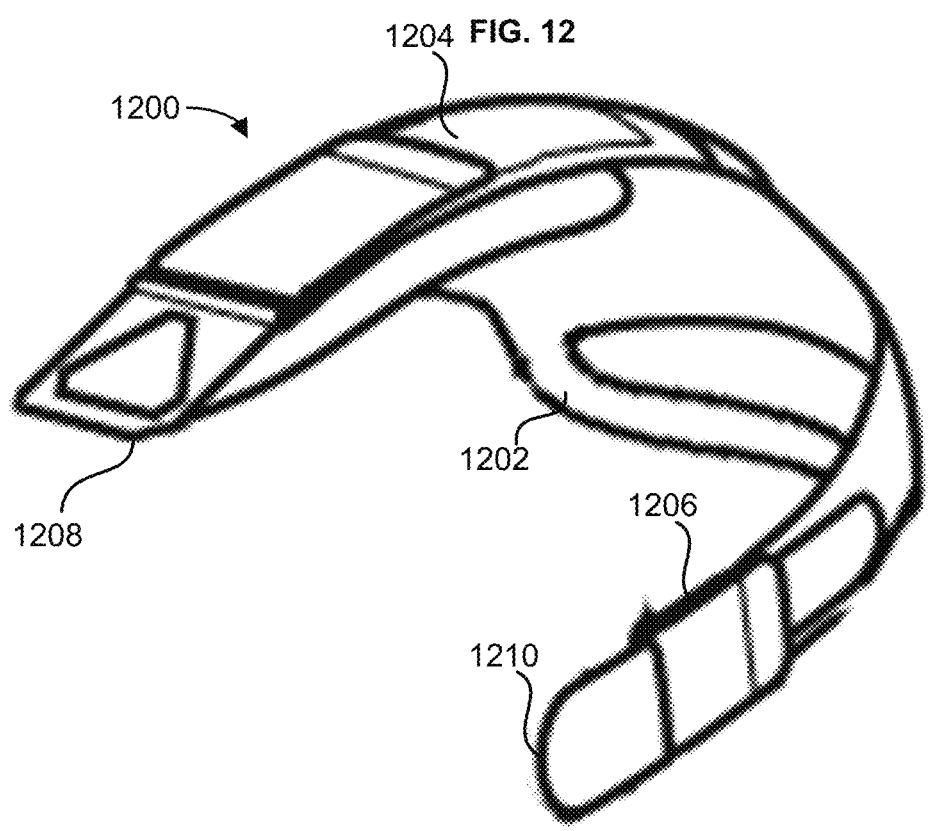

METHODS, SYSTEMS, AND APPARATUSES FOR GUIDING TRANSDUCER ARRAY PLACEMENT

CROSS-REFERENCE TO RELATED APPLICATION

This application is a national stage of International Application No. PCT/IB2020/000821 filed Oct. 7, 2020, which claims priority to U.S. Application No. 62/911,831 filed Oct. 7, 2019, which is incorporated by reference in its entirety.

BACKGROUND

Tumor Treating Fields, or TTFields, are low intensity (e.g., 1-3 V/cm) alternating electric fields within the intermediate frequency range (100-300 kHz). This non-invasive treatment targets solid tumors and is described in U.S. Pat. No. 7,565,205, which is incorporated herein by reference in its entirety. TTFields disrupt cell division through physical interactions with key molecules during mitosis. TTFields therapy is an approved mono-treatment for recurrent glioblastoma, and an approved combination therapy with chemotherapy for newly diagnosed patients. These electric fields are induced non-invasively by transducer arrays (i.e., arrays of electrodes) placed directly on the patient's scalp. TTFields also appear to be beneficial for treating tumors in other parts of the body.

SUMMARY

Described are methods comprising receiving a three dimensional (3D) transducer array placement map and generating, based on the 3D transducer array placement map, an apparatus configured to aid in placement of one or more transducer arrays on a portion of a body.

Described are apparatuses comprising a shell, contoured to fit a portion of a body, wherein the shell comprises, one or more engagement portions configured to engage one or more landmarks of the portion of the body, and one or more guide portions, wherein each of the one or more guide portions is configured to guide placement of the one or more transducer arrays, wherein engagement of the one or more landmarks by the one or more engagement portions causes the one or more guide portions to be positioned such that transducer arrays placed according to the guide portions generate a desired electric field strength in a tumor located in the portion of the body.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

To easily identify the discussion of any particular element or act, the most significant digit or digits in a reference number refer to the figure number in which that element is first introduced.

FIG. 3A and FIG. 3B illustrate an example application of the apparatus for electrotherapeutic treatment.

FIG. 12 shows an example physical apparatus that is a frame designed to aid in transducer array placement on the head.

DETAILED DESCRIPTION

Figure 1:
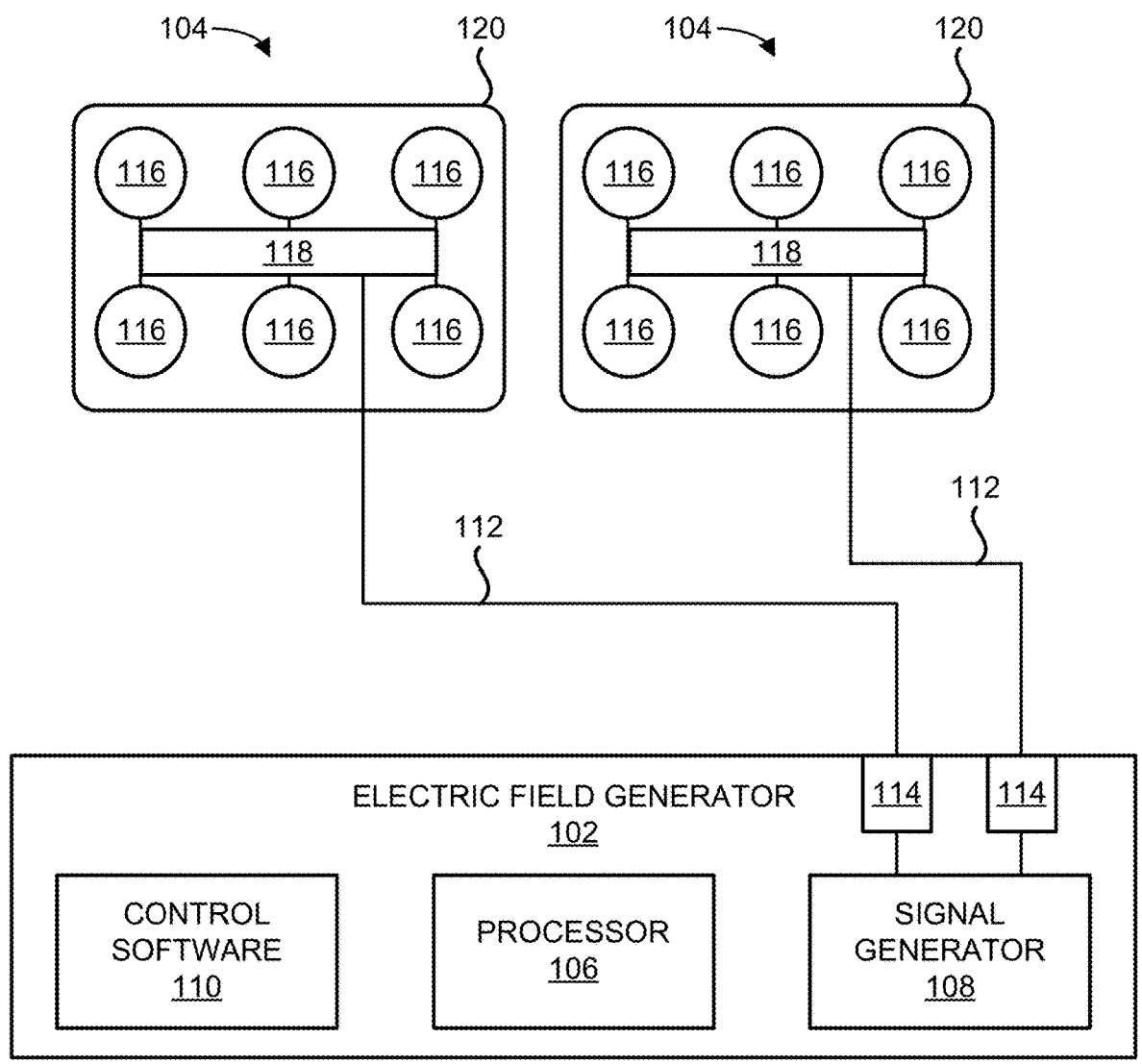
FIG. 1 shows an example apparatus for electrotherapeutic treatment.

Before the present methods and systems are disclosed and described, it is to be understood that the methods and systems are not limited to specific methods, specific components, or to particular implementations. It is also to be understood that the terminology used herein is to describe particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

TTFields, also referred to herein as alternating electric fields, are established as an anti-mitotic cancer treatment modality because they interfere with proper microtubule assembly during metaphase and eventually destroy the cells during telophase and cytokinesis. The efficacy increases with increasing field strength and the optimal frequency are cancer cell line dependent with 200 kHz being the frequency for which inhibition of glioma cell growth caused by TTFields is highest. For cancer treatment, non-invasive devices were developed with capacitively coupled transducers that are placed directly at the skin region close to the tumor. For patients with Glioblastoma Multiforme (GBM), the most common primary, malignant brain tumor in humans, the device for delivering TTFields therapy is called Optune™.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, for the Optune system, one pair of electrodes is located to the left and right (LR) of the tumor, and the other pair of electrodes is located anterior and posterior (AP) to the tumor. Cycling the field between these two directions (i.e., LR and AP) ensures that a maximal range of cell orientations is targeted.

In-vivo and in-vitro studies show that the efficacy of TTFields therapy increases as the intensity of the electric field increases. Therefore, optimizing array placement on the patient's scalp to increase the intensity in the diseased region of the brain is standard practice for the Optune system. Array placement optimization may be performed by "rule of thumb" (e.g., placing the arrays on the scalp as close to the tumor as possible), measurements describing the geometry of the patient's head, tumor dimensions, and/or tumor location. Measurements used as input may be derived from imaging data. Imaging data is intended to include any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electric field distributes within the head as a function of the positions of the array and, in some aspects, take account for variations in the electrical property distributions within the heads of different patients.

FIG. 1 shows an example apparatus 100 for electrotherapeutic treatment. Generally, the apparatus 100 may be a portable, battery or power supply operated device which produces alternating electric fields within the body by means of non-invasive surface transducer arrays. The apparatus 100 may comprise an electric field generator 102 and one or more transducer arrays 104. The apparatus 100 may be configured to generate tumor treatment fields (TTFields) (e.g., at 150 kHz) via the electric field generator 102 and deliver the TTFields to an area of the body through the one or more transducer arrays 104. The electric field generator 102 may be a battery and/or power supply operated device. In an embodiment, the one or more transducer arrays 104 are uniformly shaped. In an embodiment, the one or more transducer arrays 104 are not uniformly shaped.

The electric field generator 102 may comprise a processor 106 in communication with a signal generator 108. The electric field generator 102 may comprise control software 110 configured for controlling the performance of the processor 106 and the signal generator 108.

The signal generator 108 may generate one or more electric signals in the shape of waveforms or trains of pulses. The signal generator 108 may be configured to generate an alternating voltage waveform at frequencies in the range from about 50 kHz to about 500 kHz (preferably from about 100 kHz to about 300 kHz) (e.g., the TTFields). The voltages are such that the electric field intensity in tissue to be treated is in the range of about 0.1 V/cm to about 10 V/cm.

One or more outputs 114 of the electric field generator 102 may be coupled to one or more conductive leads 112 that are attached at one end thereof to the signal generator 108. The opposite ends of the conductive leads 112 are connected to the one or more transducer arrays 104 that are activated by the electric signals (e.g., waveforms). The conductive leads 112 may comprise standard isolated conductors with a flexible metal shield and may be grounded to prevent the spread of the electric field generated by the conductive leads 112. The one or more outputs 114 may be operated sequentially. Output parameters of the signal generator 108 may comprise, for example, an intensity of the field, a frequency of the waves (e.g., treatment frequency), and a maximum allowable temperature of the one or more transducer arrays 104. The output parameters may be set and/or determined by the control software 110 in conjunction with the processor 106. After determining a desired (e.g., optimal) treatment frequency, the control software 110 may cause the processor 106 to send a control signal the signal generator 108 that causes the signal generator 108 to output the desired treatment frequency to the one or more transducer arrays 104.

The one or more transducer arrays 104 may be configured in a variety of shapes and positions to generate an electric field of the desired configuration, direction, and intensity at a target volume to focus treatment. The one or more transducer arrays 104 may be configured to deliver two perpendicular field directions through a volume of interest.

The one or more transducer arrays 104 arrays may comprise one or more electrodes 116. The one or more electrodes 116 may be made from any material with a high dielectric constant. The one or more electrodes 116 may comprise, for example, one or more insulated ceramic discs. The electrodes 116 may be biocompatible and coupled to a flexible circuit board 118. The electrodes 116 may be configured to not come into direct contact with the skin as the electrodes 116 are separated from the skin by a layer of conductive hydrogel (not shown) (similar to that found on electrocardiogram pads).

The electrodes 116, the hydrogel, and the flexible circuit board 118 may be attached to a hypoallergenic medical adhesive bandage 120 to keep the one or more transducer arrays 104 in place on the body and in continuous direct contact with the skin. Each transducer array 104 may comprise one or more thermistors (not shown), for example, 8 thermistors, (accuracy±1° C.) to measure skin temperature beneath the transducer arrays 104. The thermistors may be configured to measure skin temperature periodically, for example, every second. The thermistors may be read by the control software 110 while the TTFields are not being delivered to avoid any interference with the temperature measurements.

If the temperature measured is below a pre-set maximum temperature (Tmax), for example, 38.5-40.0° C.±0.3° C., between two subsequent measures, the control software 110 can increase current until the current reaches maximal treatment current (for example, 4 Amps peak-to-peak). If the temperature reaches Tmax+0.3° C. and continues to rise, the control software 110 can lower the current. If the temperature rises to 41° C., the control software 110 can shut off the TTFields therapy and an overheating alarm can be triggered.

Figure 2:
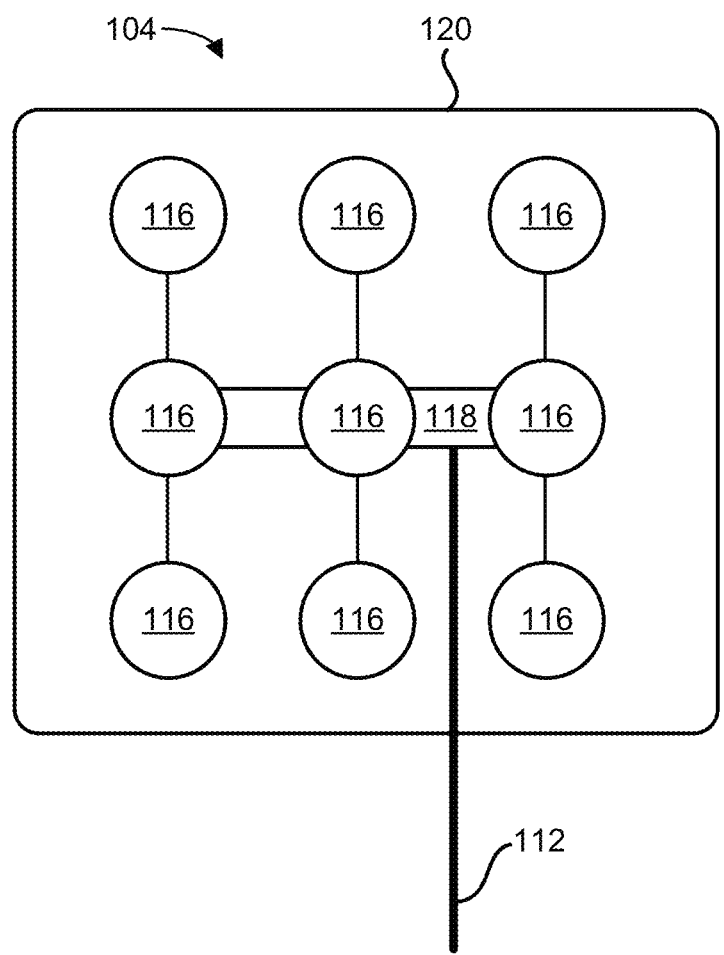
FIG. 2 shows an example transducer array.

The one or more transducer arrays 104 may vary in size and may comprise varying numbers of electrodes 116, based on patient body sizes and/or different therapeutic treatments. For example, in the context of the chest of a patient, small transducer arrays may comprise 13 electrodes each, and large transducer arrays may comprise 20 electrodes each, with the electrodes serially interconnected in each array. For example, as shown in FIG. 2, in the context of the head of a patient, each transducer array may comprise 9 electrodes each, with the electrodes serially interconnected in each array.

Alternative constructions for the one or more transducer arrays 104 are contemplated and may also be used, including, for example, transducer arrays that use ceramic elements that are not disc-shaped, and transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array would be implemented using a region of a conductive material that is configured for placement against a subject/patient's body, with no insulating dielectric layer disposed between the conductive elements and the body. Other alternative constructions for implementing the transducer arrays may also be used. Any transducer array (or similar device/component) configuration, arrangement, type, and/or the like may be used for the methods and systems described herein as long as the transducer array (or similar device/component) configuration, arrangement, type, and/or the like is (a) capable of delivering TTFields to a subject/patient's body and (b) and may be positioned arranged, and/or placed on a portion of a patient/subject's body as described herein.

Status of the apparatus 100 and monitored parameters may be stored a memory (not shown) and can be transferred to a computing device over a wired or wireless connection.

The apparatus 100 may comprise a display (not shown) for displaying visual indicators, such as power on, treatment on, alarms, and low battery.

FIG. 3A and FIG. 3B show an example application of the apparatus 100. A transducer array 104a and a transducer array 104b are shown, each incorporated into a hypoallergenic medical adhesive bandage 120a and 120b, respectively. The hypoallergenic medical adhesive bandages 120a and 120b are applied to skin surface 302. A tumor 304 is located below the skin surface 302 and bone tissue 306 and is located within brain tissue 308. The electric field generator 102 causes the transducer array 104a and the transducer array 104b to generate alternating electric fields 310 within the brain tissue 308 that disrupt rapid cell division exhibited by cancer cells of the tumor 304. The alternating electric fields 310 have been shown in non-clinical experiments to arrest the proliferation of tumor cells and/or to destroy them. Use of the alternating electric fields 310 takes advantage of the special characteristics, geometrical shape, and rate of dividing cancer cells, which make them susceptible to the effects of the alternating electric fields 310. The alternating electric fields 310 alter their polarity at an intermediate frequency (on the order of 100-300 kHz). The frequency used for a particular treatment may be specific to the cell type being treated (e.g., 150 kHz for MPM). The alternating electric fields 310 have been shown to disrupt mitotic spindle microtubule assembly and to lead to dielectrophoretic dislocation of intracellular macromolecules and organelles during cytokinesis. These processes lead to physical disruption of the cell membrane and to programmed cell death (apoptosis).

Because the effect of the alternating electric fields 310 is directional with cells dividing parallel to the field affected more than cells dividing in other directions, and because cells divide in all directions, alternating electric fields 310 may be delivered through two pairs of transducer arrays 104 that generate perpendicular fields within the treated tumor. More specifically, one pair of transducer arrays 104 may be located to the left and right (LR) of the tumor, and the other pair of transducer arrays 104 may be located anterior and posterior (AP) to the tumor. Cycling the alternating electric fields 310 between these two directions (e.g., LR and AP) ensures that a maximal range of cell orientations is targeted. In an embodiment, the alternating electric fields 310 may be delivered according to a symmetric setup of transducer arrays 104 (e.g., four total transducer arrays 104, two matched pairs). In another embodiment, the alternating electric fields 310 may be delivered according to an asymmetric setup of transducer arrays 104 (e.g., three total transducer arrays 104). An asymmetric setup of transducer arrays 104 may engage two of the three transducer arrays 104 to deliver the alternating electric fields 310 and then switch to another two of the three transducer arrays 104 to deliver the alternating electric fields 310, and the like.

In-vivo and in-vitro studies show that the efficacy of TTFields therapy increases as the intensity of the electric field increases. The methods, systems, and apparatuses described are configured for optimizing array placement on the patient's scalp to increase the intensity in the diseased region of the brain.

Figure 4A:
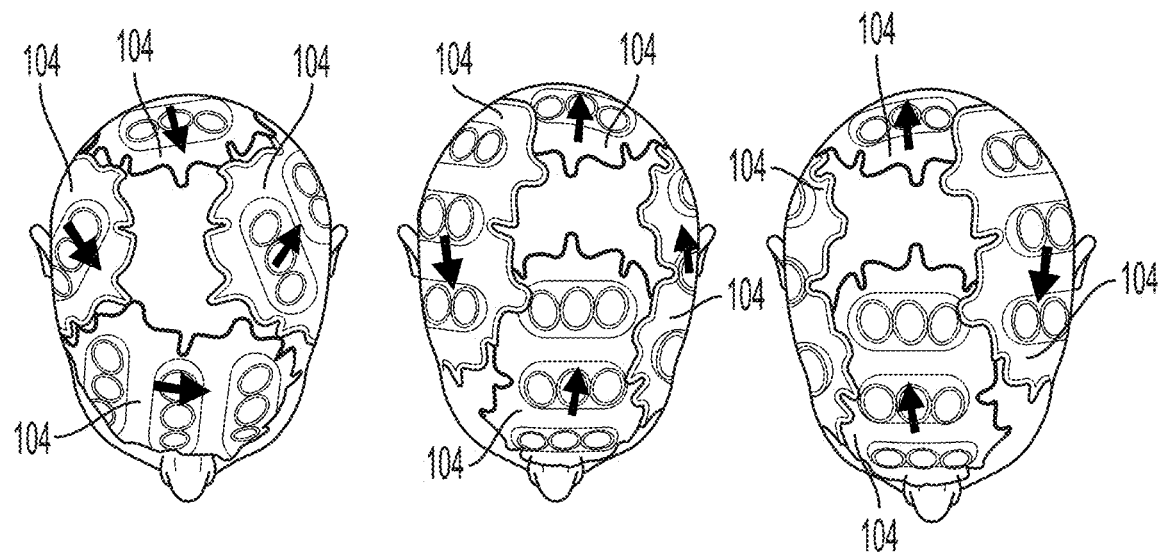
FIG. 4A shows transducer arrays placed on a patient's head.
Figure 4B:
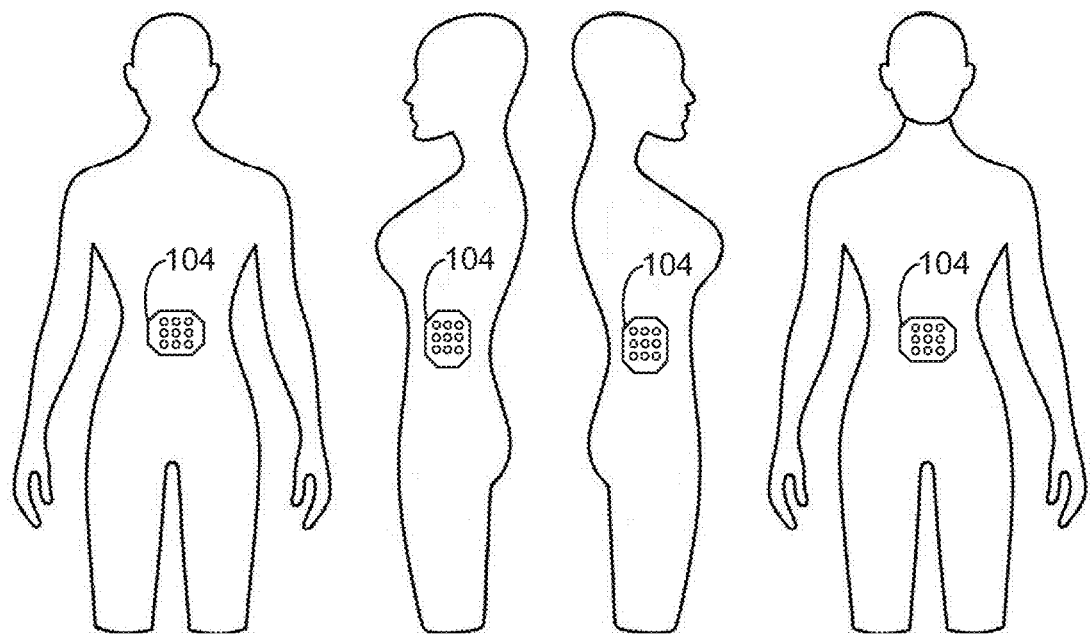
FIG. 4B shows transducer arrays placed on a patient's abdomen.
Figure 5A:
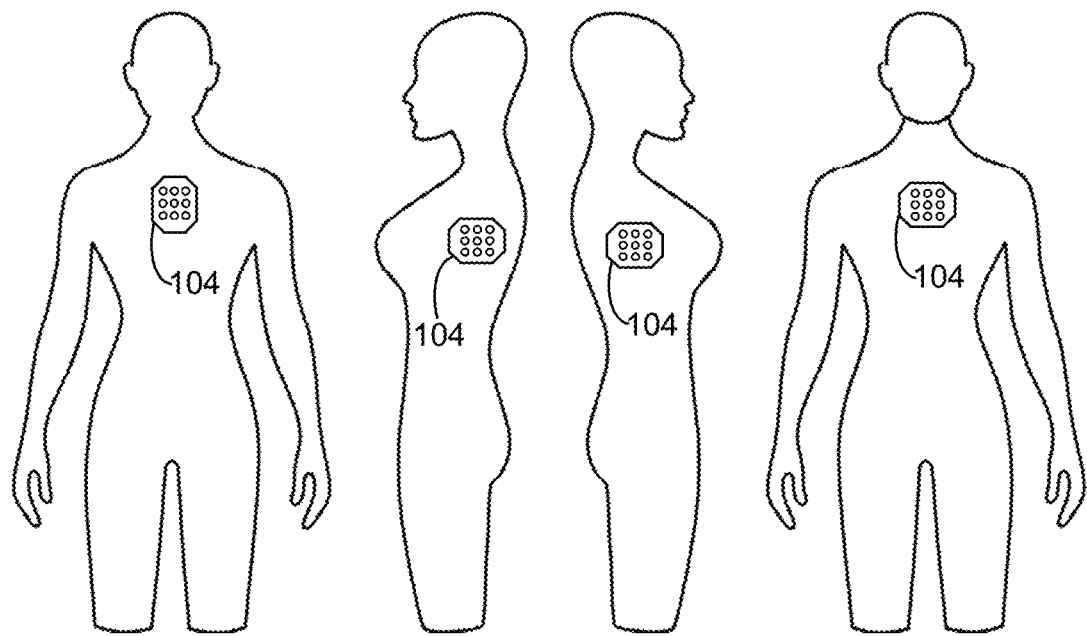
FIG. 5A shows the transducer arrays placed on a patient's torso.
Figure 5B:
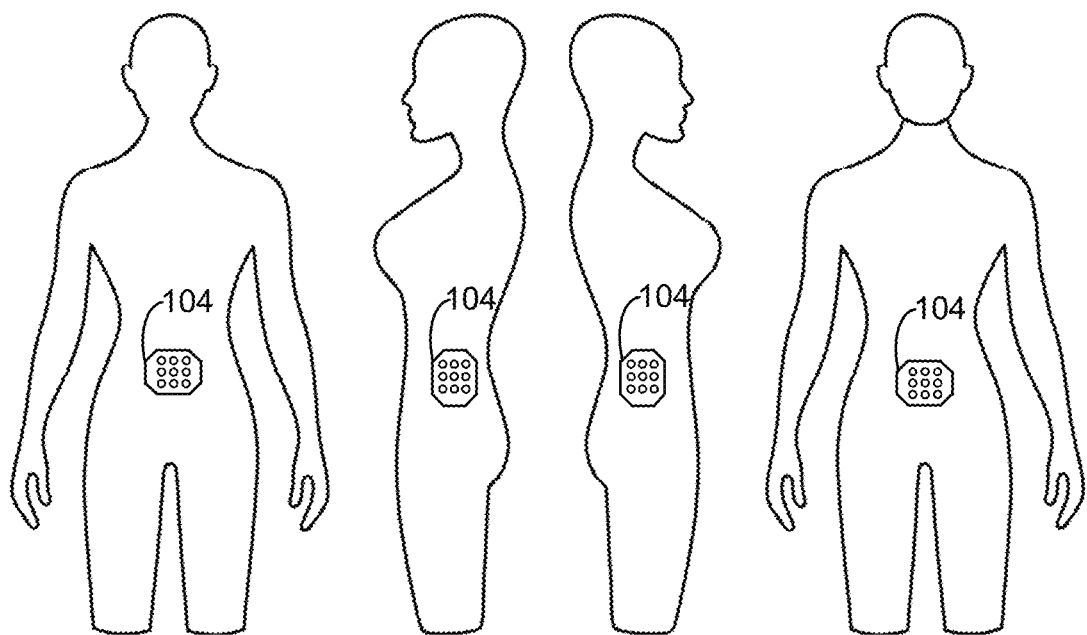
FIG. 5B shows transducer arrays placed on a patient's pelvis

As shown in FIG. 4A, the transducer arrays 104 may be placed on a patient's head. As shown in FIG. 4B, the transducer arrays 104 may be placed on a patient's abdomen. As shown in FIG. 5A, the transducer arrays 104 may be placed on a patient's torso. As shown in FIG. 5B, the transducer arrays 104 may be placed on a patient's pelvis. Placement of the transducer arrays 104 on other portions of a patient's body (e.g., arm, leg, etc.) are specifically contemplated.

Figure 6:
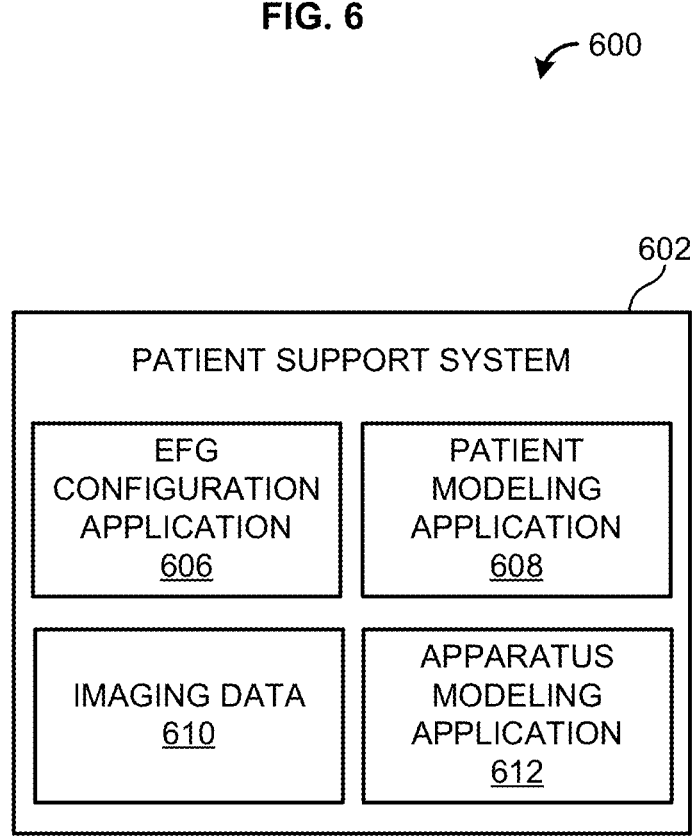
FIG. 6 is a block diagram depicting an electric field generator and a patient support system.

FIG. 6 is a block diagram depicting non-limiting examples of a system 100 comprising a patient support system 602. The patient support system 602 can comprise one or multiple computers configured to operate and/or store an electric field generator (EFG) configuration application 606, a patient modeling application 608, imaging data 610, and/or an apparatus modeling application 612. The patient support system 602 can comprise, for example, a computing device. The patient support system 602 can comprise, for example, a laptop computer, a desktop computer, a mobile phone (e.g., a smartphone), a tablet, and the like.

The patient modeling application 608 may be configured to generate a three dimensional model of a portion of a body of a patient (e.g., a patient model) according to the imaging data 610. The imaging data 610 may comprise any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). The patient modeling application 608 may also be configured to generate a three-dimensional array layout map based on the patient model and one or more electric field simulations. The apparatus modeling application 612 may be configured to generate a 2-D or 3-D model of an apparatus configured for guiding placement of one or more transducer arrays, according to the three-dimensional array layout map.

Figure 7:
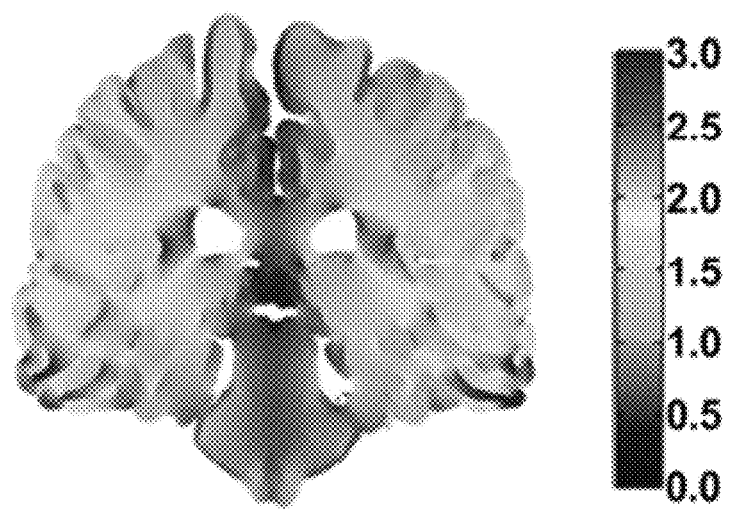
FIG. 7 illustrates electric field magnitude and distribution (in V/cm) shown in coronal view from a finite element method simulation model.

To properly optimize array placement on a portion of a patient's body, the imaging data 610, such as MRI imaging data, may be analyzed by the patient modeling application 608 to identify a region of interest that comprises a tumor. In the context of a patient's head, to characterize how electric fields behave and distribute within the human head, modeling frameworks based on anatomical head models using Finite Element Method (FEM) simulations may be used. These simulations yield realistic head models based on magnetic resonance imaging (MRI) measurements and compartmentalize tissue types such as a skull, white matter, gray matter, and cerebrospinal fluid (CSF) within the head. Each tissue type may be assigned dielectric properties for relative conductivity and permittivity, and simulations may be run whereby different transducer array configurations are applied to the surface of the model to understand how an externally applied electric field, of preset frequency, will distribute throughout any portion of a patient's body, for example, the brain. The results of these simulations, employing paired array configurations, a constant current, and a preset frequency of 200 kHz, have demonstrated that electric field distributions are relatively non-uniform throughout the brain and that electric field intensities exceeding 1 V/cm are generated in most tissue compartments except CSF. These results are obtained assuming total currents with a peak-to-peak value of 1800 milliamperes (mA) at the transducer array-scalp interface. This threshold of electric field intensity is sufficient to arrest cellular proliferation in glioblastoma cell lines. Additionally, by manipulating the configuration of paired transducer arrays, it is possible to achieve an almost tripling of electric field intensity to a particular region of the brain as shown in FIG. 7. FIG. 7 illustrates electric field magnitude and distribution (in V/cm) shown in the coronal view from a finite element method simulation model. This simulation employs a left-right paired transducer array configuration.

Figure 8A:
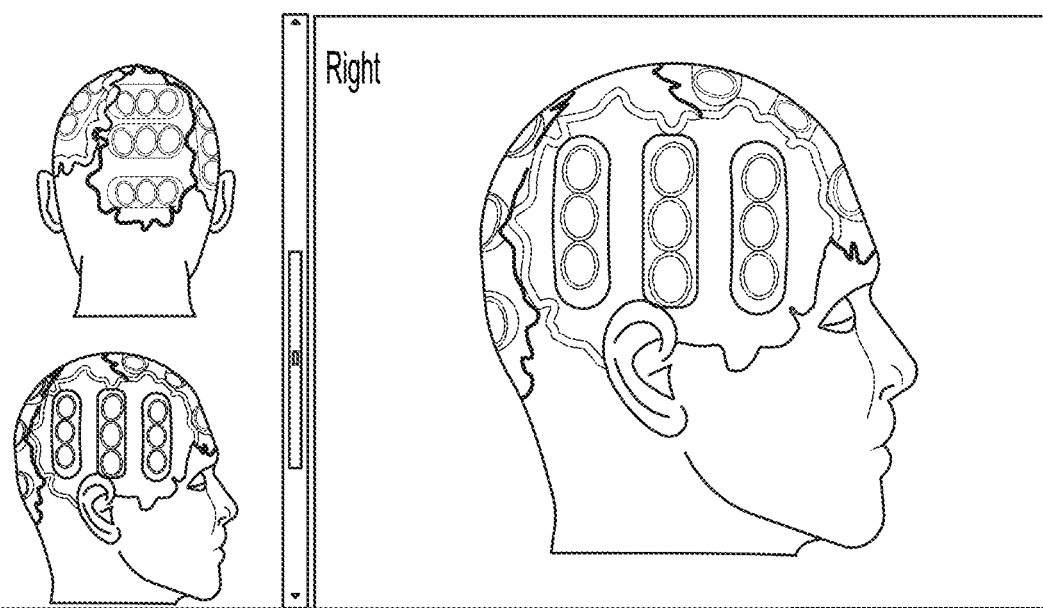
FIG. 8A shows a three-dimensional array layout map 800.
Figure 8B:
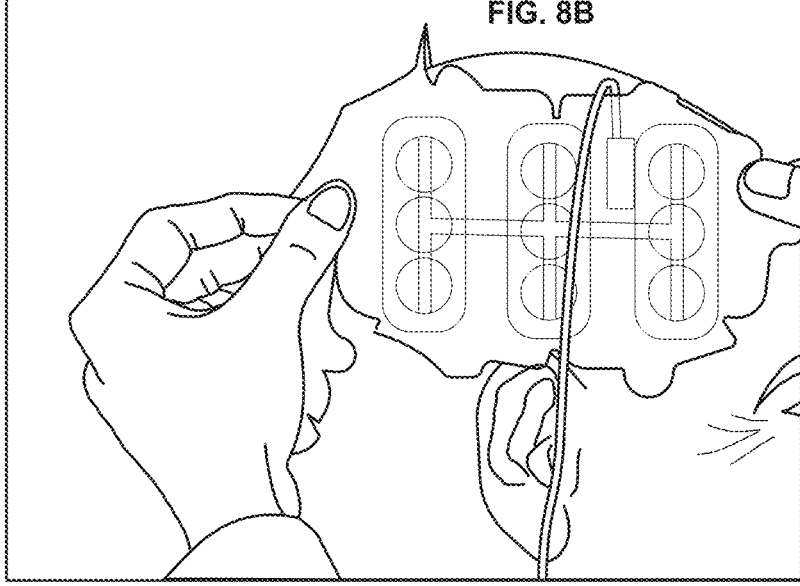
FIG. 8B shows placement of tranducer arrays on the scalp of a patient.

In an aspect, the patient modeling application 608 may be configured to determine a desired (e.g., optimal) transducer array layout for a patient based on the location and extent of the tumor. For example, initial morphometric head size measurements may be determined from the T1 sequences of a brain MRI, using axial and coronal views. Postcontrast axial and coronal MRI slices may be selected to demonstrate the maximal diameter of enhancing lesions. Employing measures of head size and distances from predetermined fiducial markers to tumor margins, varying permutations, and combinations of paired array layouts may be assessed to generate the configuration which delivers maximal electric field intensity to the tumor site. As shown in FIG. 8A, the output may be a three-dimensional array layout map 800. The three-dimensional array layout map 800 may be used by the patient and/or caregiver in arranging arrays on the scalp during the normal course of TTFields therapy as shown in FIG. 8B.

In an aspect, the patient modeling application 608 can be configured to determine the three-dimensional array layout map for a patient. MRI measurements of the portion of the patient that is to receive the transducer arrays may be determined. By way of example, the MRI measurements may be received via a standard Digital Imaging and Communications in Medicine (DICOM) viewer. MRI measurement determination may be performed automatically, for example by way of artificial intelligence techniques, or may be performed manually, for example by way of a physician.

Figure 9A:
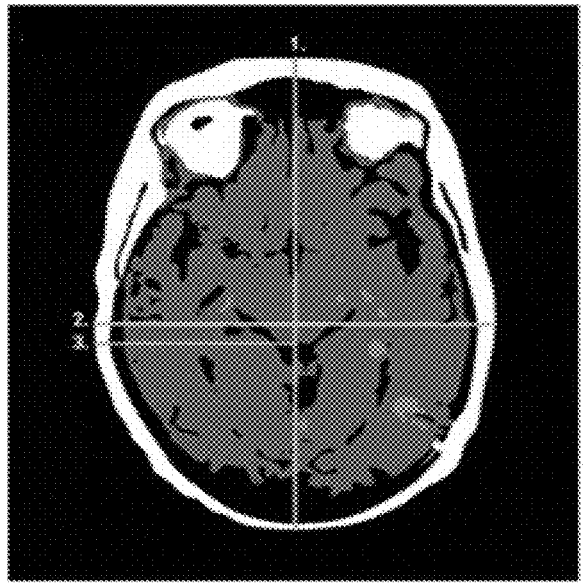
FIG. 9A shows an axial T1 sequence slice containing most apical image, including orbits used to measure head size.
Figure 9B:
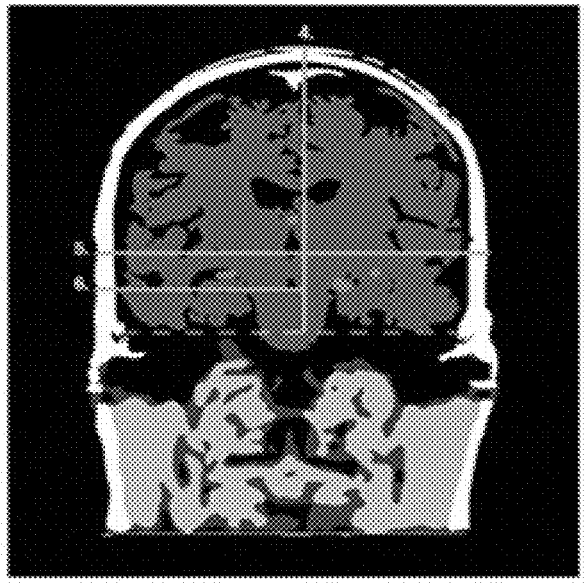
FIG. 9B shows a coronal T1 sequence slice selecting image at level of ear canal used to measure head size.
Figure 9C:
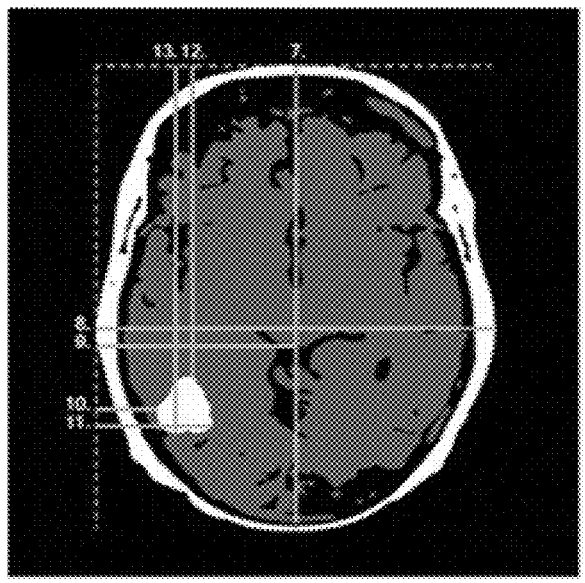
FIG. 9C shows a postcontrast T1 axial image shows maximal enhancing tumor diameter used to measure tumor location.
Figure 9D:
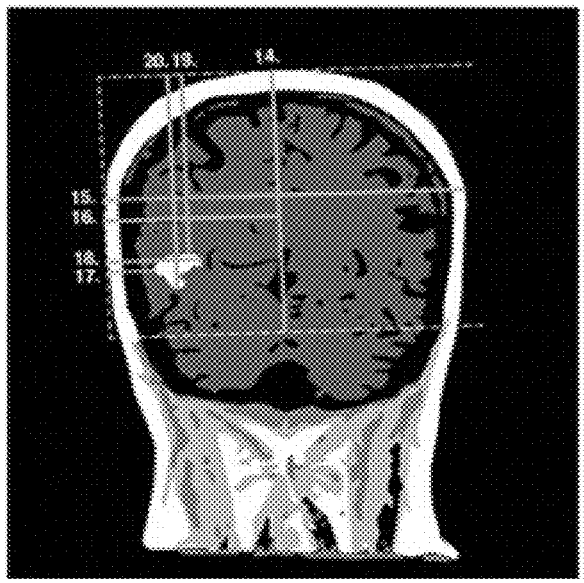
FIG. 9D shows a postcontrast T1 coronal image shows maximal enhancing tumor diameter used to measure tumor location.

Manual MRI measurement determination may comprise receiving and/or providing MRI data via a DICOM viewer. The MRI data may comprise scans of the portion of the patient that contains a tumor. By way of example, in the context of the head of a patient, the MRI data may comprise scans of the head that comprise one or more of a right frontotemporal tumor, a right parieto-temporal tumor, a left frontotemporal tumor, a left parieto-occipital tumor, and/or a multi-focal midline tumor. FIG. 9A, FIG. 9B, FIG. 9C, and FIG. 9D show example MRI data showing scans of the head of a patient. FIG. 9A shows an axial T1 sequence slice containing the most apical image, including orbits used to measure head size. FIG. 9B shows a coronal T1 sequence slice selecting image at the level of the ear canal used to measure head size. FIG. 9C shows a postcontrast T1 axial image shows maximal enhancing tumor diameter used to measure tumor location. FIG. 9D shows a postcontrast T1 coronal image shows maximal enhancing tumor diameter used to measure tumor location. MRI measurements may commence from fiducial markers at the outer margin of the scalp and extend tangentially from a right-, anterior-, superior origin. Morphometric head size may be estimated from the axial T1 MRI sequence selecting the most apical image which still included the orbits (or the image directly above the superior edge of the orbits)

In an aspect, the MRI measurements may comprise, for example, one or more of, head size measurements and/or tumor measurements. In an aspect, one or more MRI measurements may be rounded to the nearest millimeter and may be provided to a transducer array placement module (e.g., software) for analysis. The MRI measurements may then be used to generate the three-dimensional array layout map (e.g., three-dimensional array layout map 800).

The MRI measurements may comprise one or more head size measurements such as a maximal anteroposterior (A-P) head size, commencing measurement from the outer margin of the scalp; a maximal width of the head perpendicular to the A-P measurement: the right to left lateral distance; and/or a distance from the far most right margin of the scalp to the anatomical midline.

The MRI measurements may comprise one or more head size measurements such as coronal view head size measurements. Coronal view head size measurements may be obtained on the T1 MRI sequence selecting the image at the level of the ear canal (FIG. 9B). The coronal view head size measurements may comprise one or more of: a vertical measurement from the apex of the scalp to an orthogonal line delineating the inferior margin of the temporal lobes; a maximal right to left lateral head width; and/or a distance from the far right margin of the scalp to the anatomical midline.

The MRI measurements may comprise one or more tumor measurements, such as tumor location measurements. The tumor location measurements may be made using T1 postcontrast MRI sequences, firstly on the axial image demonstrating maximal enhancing tumor diameter (FIG. 9C). The tumor location measurements may comprise one or more of: a maximal A-P head size, excluding the nose; a maximal right to left lateral diameter, measured perpendicular to the A-P distance; a distance from the right margin of the scalp to the anatomical midline; a distance from the right margin of the scalp to the closest tumor margin, measured parallel to the right-left lateral distance and perpendicular to the A-P measurement; a distance from the right margin of the scalp to the farthest tumor margin, measured parallel to the right-left lateral distance, perpendicular to the A-P measurement; a distance from the front of the head, measured parallel to the A-P measurement, to the closest tumor margin; and/or a distance from the front of the head, measured parallel to the A-P measurement, to the farthest tumor margin.

The one or more tumor measurements may comprise coronal view tumor measurements. The coronal view tumor measurements may comprise identifying the postcontrast T1 MRI slice featuring the maximal diameter of tumor enhancement (FIG. 9D). The coronal view tumor measurements may comprise one or more of: a maximal distance from the apex of the scalp to the inferior margin of the cerebrum. In anterior slices, this would be demarcated by a horizontal line drawn at the inferior margin of the frontal or temporal lobes, and posteriorly, it would extend to the lowest level of visible tentorium; a maximal right to left lateral head width; a distance from the right margin of the scalp to the anatomical midline; a distance from the right margin of the scalp to the closest tumor margin, measured parallel to the right-left lateral distance; a distance from the right margin of the scalp to the farthest tumor margin, measured parallel to the right-left lateral distance; a distance from the apex of the head to the closest tumor margin, measured parallel to the superior apex to inferior cerebrum line; and/or a distance from the apex of the head to the farthest tumor margin, measured parallel to the superior apex to inferior cerebrum line.

Other MRI measurements may be used, particularly when the tumor is present in another portion of the patient's body.

The MRI measurements may be used by the patient modeling application 608 to generate a patient model. The patient model may then be used to determine the three-dimensional array layout map (e.g., three-dimensional array layout map 800). Continuing the example of a tumor within the head of a patient, a healthy head model may be generated which serves as a deformable template from which patient models can be created. When creating a patient model, the tumor may be segmented from the patient's MRI data (e.g., the one or more MRI measurements). Segmenting the MRI data identifies the tissue type in each voxel, and electric properties may be assigned to each tissue type based on empirical data. Table 1 shows the standard electrical properties of tissues that may be used in simulations. The region of the tumor in the patient MRI data may be masked, and non-rigid registration algorithms may be used to register the remaining regions of the patient head on to a 3D discrete image representing the deformable template of the healthy head model. This process yields a non-rigid transformation that maps the healthy portion of the patient's head into the template space, as well as the inverse transformation that maps the template into the patient space. The inverse transformation is applied to the 3D deformable template to yield an approximation of the patient's head in the absence of a tumor. Finally, the tumor is planted back into the deformed template to yield the full patient model. The patient model may be a digital representation in three-dimensional space of the portion of the patient's body, including internal structures, such as tissues, organs, tumors, etc.

TABLE 1

| Tissue Type | Conductivity, S/m | Relative Permittivity |
|---|---|---|
| Scalp | 0.3 | 5000 |
| Skull | 0.08 | 200 |
| Cerebrospinal fluid | 1.79 | 110 |
| Gray matter | 0.25 | 3000 |
| White matter | 0.12 | 2000 |
| Enhancing tumor | 0.24 | 2000 |
| Enhancing nontumor | 0.36 | 1170 |
| Resection cavity | 1.79 | 110 |
| Necrotic tumor | 1 | 110 |
| Hematoma | 0.3 | 2000 |
| Ischemia | 0.18 | 2500 |
| Atrophy | 1 | 110 |
| Air | 0 | 0 |

Delivery of TTFields may then be simulated by the patient modeling application 608 using the patient model. To ensure systematic positioning of the transducer arrays relative to the tumor location, a reference coordinate system may be defined. For example, a transversal plane may initially be defined by conventional LR and AP positioning of the transducer arrays. The left-right direction may be defined as the x-axis, the AP direction may be defined as the y-axis, and the craniocaudal direction normal to the XY-plane may be defined as the Z-axis.

After defining the coordinate system, transducer arrays may be virtually placed on the patient model with their centers and longitudinal axes in the XY-plane. A pair of transducer arrays may be systematically rotated around the z-axis of the head model, i.e. in the XY-plane, from 0 to 180 degrees, thereby covering the entire circumference of the head (by symmetry). The rotation interval may be, for example, 15 degrees, corresponding to approximately 2 cm translations, giving a total of twelve different positions in the range of 180 degrees. Other rotation intervals are contemplated. Electric field distribution calculations may be performed for each transducer array position relative to tumor coordinates.

Electric field distribution in the patient model may be determined by the patient modeling application 608 using a finite element (FE) approximation of electrical potential. In general, the quantities defining a time-varying electromagnetic field are given by the complex Maxwell equations. However, in biological tissues and at the low to an intermediate frequency of TTFields (f=200 kHz), the electromagnetic wavelength is much larger than the size of the head and the electric permittivity $\epsilon$ is negligible compared to the real-valued electric conductivity $\sigma$, i.e., where $\omega=2\pi f$ is the angular frequency. This implies that the electromagnetic propagation effects and capacitive effects in the tissue are negligible, so the scalar electric potential may be well approximated by the static Laplace equation $\nabla \cdot (\sigma \nabla \phi)=0$, with appropriate boundary conditions at the electrodes and skin. Thus, the complex impedance is treated as resistive (i.e. reactance is negligible) and currents flowing within the volume conductor are, therefore, mainly free (Ohmic) currents. The FE approximation of Laplace's equation was calculated using the SimNIBS software (simnibs.org). Computations were based on the Galerkin method and the residuals for the conjugate gradient solver were required to be <1E-9. Dirichlet boundary conditions were used with the electric potential was set to (arbitrarily chosen) fixed values at each set of electrode arrays. The electric (vector) field was calculated as the numerical gradient of the electric potential and the current density (vector field) was computed from the electric field using Ohm's law. The potential difference of the electric field values and the current densities were linearly rescaled to ensure a total peak-to-peak amplitude for each array pair of 1.8 A, calculated as the (numerical) surface integral of the normal current density components overall triangular surface elements on the active electrode discs. This corresponds to the current level used for clinical TTFields therapy by the Optune® device. The "dose" of TTFields was calculated as the intensity (L2 norm) of the field vectors. The modeled current is assumed to be provided by two separate and sequentially active sources each connected to a pair of 3×3 transducer arrays. The left and posterior arrays may be defined to be sources in the simulations, while the right and anterior arrays were the corresponding sinks, respectively. However, as TTFields employ alternating fields, this choice is arbitrary and does not influence the results.

An average electric field strength generated by transducer arrays placed at multiple locations on the patient may be determined by the patient modeling application 608 for one or more tissue types. In an aspect, the transducer array position that corresponds to the highest average electric field strength in the tumor tissue type(s) may be selected as a desired (e.g., optimal) transducer array position for the patient. In another aspect, one or more candidate positions for a transducer array(s) may be excluded as a result of a physical condition of the patient. For example, one or more candidate positions may be excluded based on areas of skin irritation, scars, surgical sites, discomfort, etc. Accordingly, the transducer array position that corresponds to the highest average electric field strength in the tumor tissue type(s), after excluding one or more candidate positions, may be selected as a desired (e.g., optimal) transducer array position for the patient. Thus, a transducer array position may be selected that results in less than the maximum possible average electric field strength.

The patient model may be modified to include an indication of the desired transducer array position. The resulting patient model, comprising the indication(s) of the desired transducer array position(s), may be referred to as the three-dimensional array layout map (e.g., three-dimensional array layout map 600). The three-dimensional array layout map may thus comprise a digital representation, in three-dimensional space, of the portion of the patient's body, an indication of tumor location, an indication of a position for placement of one or more transducer arrays, combinations thereof, and the like.

The three-dimensional array layout map may be provided to the patient in a digital form and/or a physical form. The patient, and/or a patient caregiver, may use the three-dimensional array layout map to affix one or more transducer arrays to an associated portion of the patient's body (e.g., head).

The three-dimensional array layout map may further comprise an indication of one or more landmarks on the portion of the patient's body (e.g., curves, bumps, crevices, structures (e.g., ear, nose, nipple, etc.). The indication of one or more landmarks on the portion of the patient's body may be derived by the patient modeling application 608 from the imaging data. The three-dimensional array layout map may comprise position data indicative of the placement of the one or more transducer arrays on the portion of the body and surface data indicative of one or more landmarks of the portion of the body. Digital three dimensional representation can be used as described in Bücking T M, et al. (2017), From medical imaging data to 3D printed anatomical models. PLoS ONE 12(5): e0178540; Ahmed Hosny et al. J Thorac Cardiovasc Surg 2018, 155:143-5, incorporated by reference herein.

In an aspect, the three-dimensional array layout map may be used by the apparatus modeling application 612 to generate a physical apparatus to aid in the placement of the transducer arrays on the patient's body. The physical apparatus may be made of any material, such as leather, cloth, plastic, paper, metal, and the like. The physical apparatus may be contoured to fit the portion of the patient's body where the transducer arrays are to be affixed. The physical apparatus may be configured to guide placement of the transducer arrays according to a symmetrical setup or an asymmetrical setup. In an embodiment, the apparatus may only need to be generated for placement of one or two transducer arrays, for example, to aid in the placement of transducer arrays in difficult to see and/or reach areas of the patient's body.

In an embodiment, the apparatus for guiding placement of one or more transducer arrays may be customized to a specific individual. In a further embodiment, the apparatus may be semi-customized. For example, the apparatus may be generated according to a variety of standard sizes. For example, the apparatus may be sized according to a women's or men's small, medium, large, extra-large, extra-extra-large, and the like.

Figure 10:
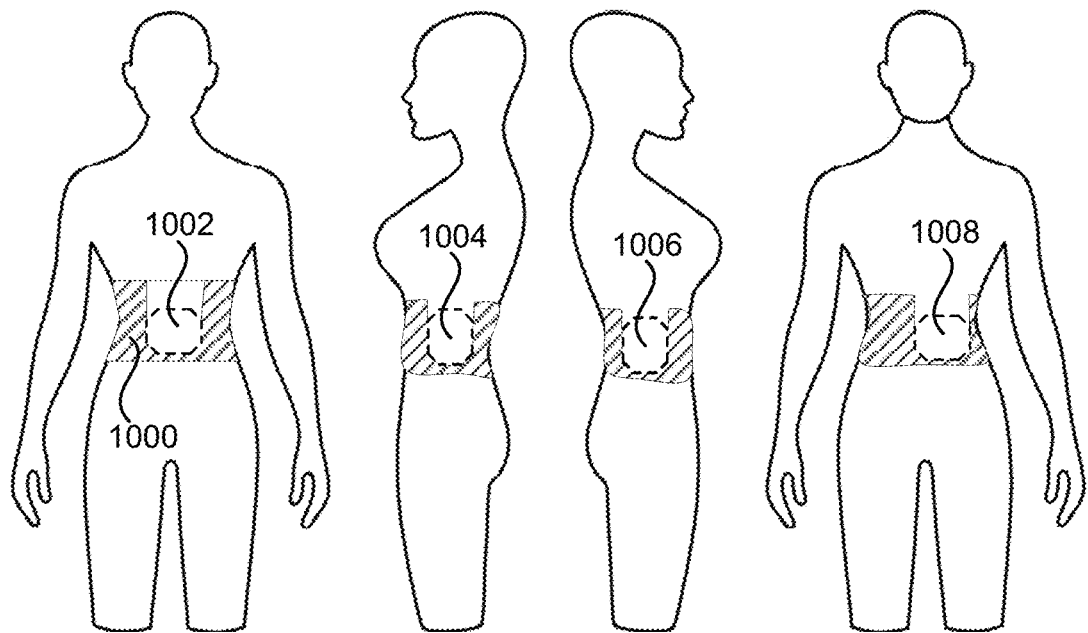
FIG. 10 shows an example physical apparatus that is designed to aid in transducer array placement on the abdomen.
Figure 11A:
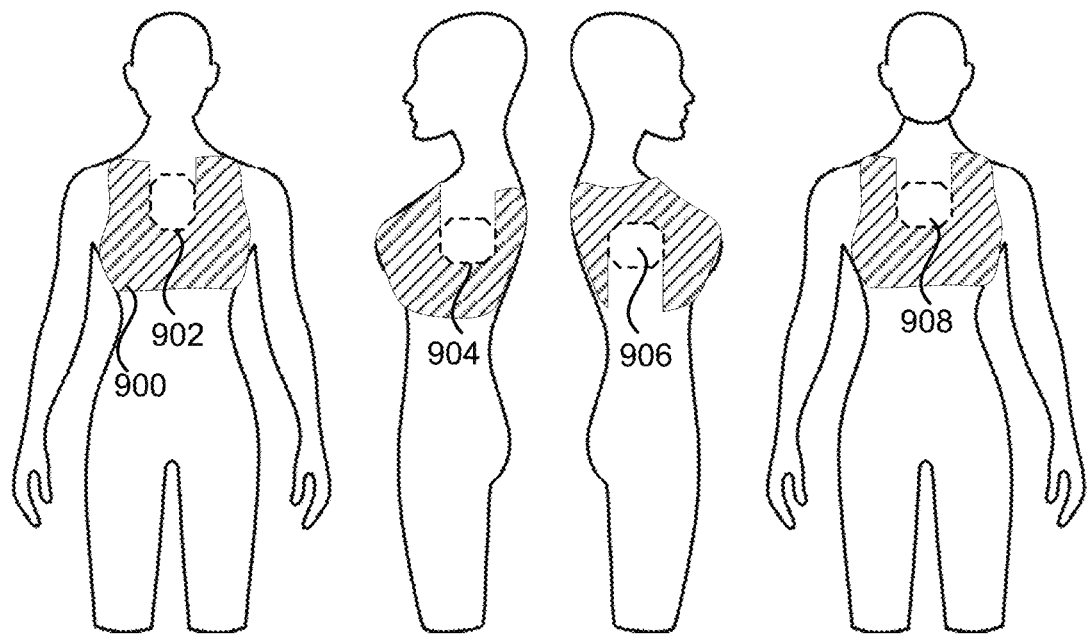
FIG. 11A shows an example physical apparatus that is designed to aid in transducer array placement on the torso.
Figure 11B:
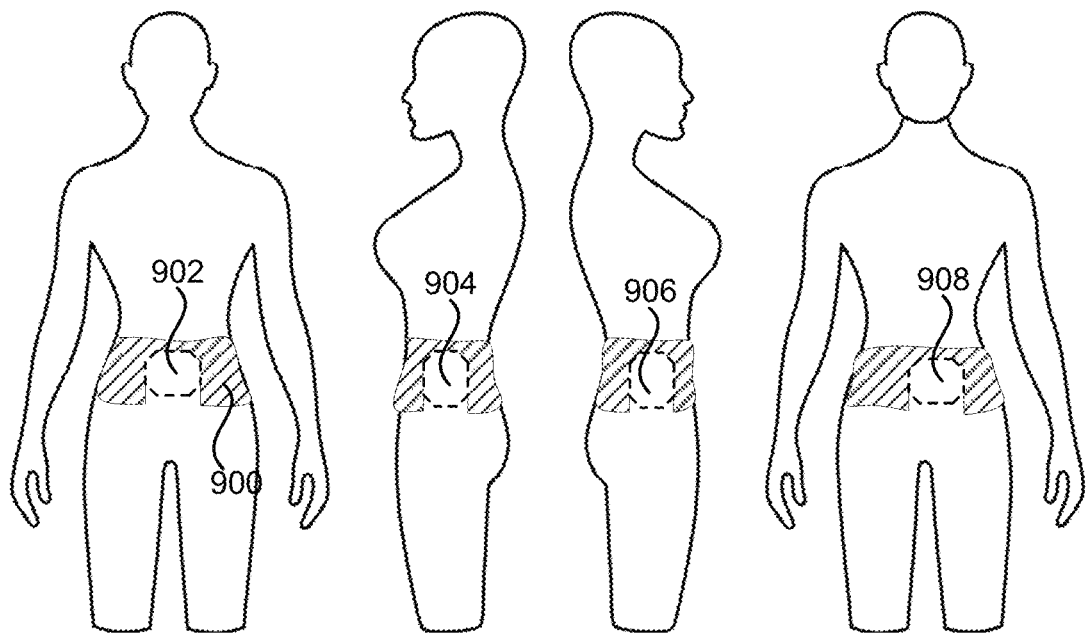
FIG. 11B shows an example physical apparatus that is designed to aid in transducer array placement on the pelvis.
Figure 13A:
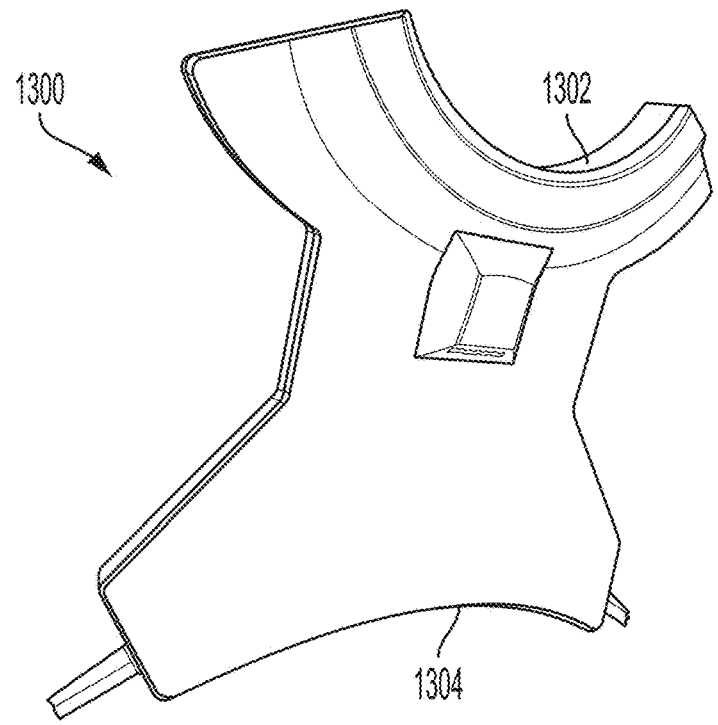
FIG. 13A shows a first view of an example 3D model of a physical apparatus that is a designed to aid in transducer array placement on the side of a torso.
Figure 13B:
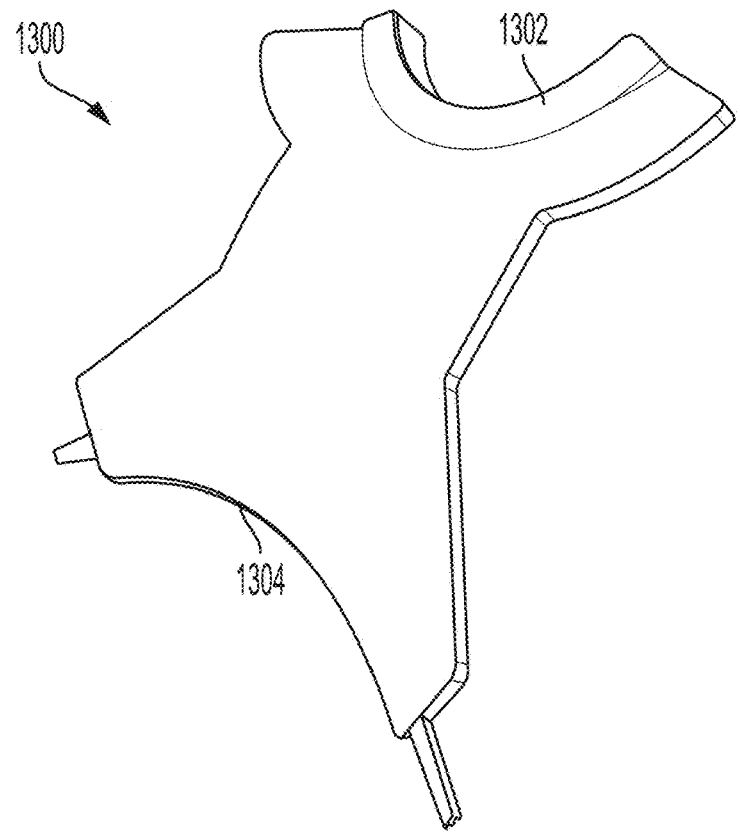
FIG. 13B shows a second view of the example 3D model of a physical apparatus that is a designed to aid in transducer array placement on the side of a torso.

FIG. 10 shows an example physical apparatus that is designed to aid in transducer array placement on the abdomen. The physical apparatus may be placed on the abdomen, the transducer array may be placed on the abdomen via an opening in the physical apparatus, and the physical apparatus may be removed before treatment. FIG. 11A shows an example physical apparatus that is designed to aid in transducer array placement on the torso. The physical apparatus may be placed on the torso, the transducer array may be placed on the torso via an opening in the physical apparatus, and the physical apparatus may be removed before treatment. FIG. 11B shows an example physical apparatus that is designed to aid in transducer array placement on the pelvis. The physical apparatus may be placed on the pelvis, the transducer array may be placed on the pelvis via an opening in the physical apparatus, and the physical apparatus may be removed before treatment. FIG. 12 shows an example physical apparatus that is a frame designed to aid in transducer array placement on the head. FIG. 13A and FIG. 13B shows an example 3D model of a physical apparatus that is designed to aid in transducer array placement on the side of a torso.

In an aspect, the physical apparatus may be configured for placement of one or more transducer arrays. In some aspects, each transducer array may b e associated with one physical apparatus. In other aspects, a pair of transducer arrays may be associated with one physical apparatus. The physical apparatus may comprise one or more engagement portions configured to align and/or engage one or more landmarks of the portion of the body. The one or more engagement portions may comprise one or more of, a hole, a slot, a slit, an opening, a curve, a dimple, an angle, a hook, a strap, a buckle, an adhesive, combinations thereof, and the like.

The physical apparatus may comprise one or more guide portions. The one or more guide portions are reference points that guide the placement of transducer arrays on the body. The one or more guide portions, in contrast to the one or more engagement portions, are configured to align and/or engage the transducer array, rather than a landmark. The one or more guide portions may be indicative of a position for each transducer array to generate an electric field having a desired strength in a tumor located in the portion of the body. The one or more guide portions may be shaped to guide the placement of one or more transducer arrays. The one or more guide portions may be associated with an area of proper transducer array placement, as derived from the three-dimensional array layout map for the patient. The one or more guide portions may be approximately the same size and shape as a transducer array. The one or more guide portions may be a size and/or shape of a portion of a transducer array, for example, a corner of the transducer array, a quarter of the shape of the transducer array, a third of the shape of the transducer array, half of the shape of the transducer array, and the like. The one or more guide portions may be a cutout of the apparatus, such as a hole, a cap, a curve, and the like. The one or more guide portions may comprise an indication that references a specific transducer array to be placed with a specific transducer array. For example, the one or more guide portions may comprise a marking, such as an arrow, a word, a number, a graphic, a color, and the like, to assist in the placement of the transducer arrays. In an aspect, the one or more guide portions may be color-coded to match a specific transducer array. For example, a guide portion may be outlined or otherwise colored red, and a corresponding transducer array may be outlined or otherwise colored red to indicate that that transducer array should be placed within that guide portion. The one or more guide portions may comprise one or m ore distinctive physical characteristics to aid in the placement of the transducer arrays in situations where the guide portion is not visible to the patient. For example, the one or more guide portions may comprise a ridge, a bump, or other tactile features that the patient may feel and use to guide placement of the transducer array within the guide portion.

In an embodiment, each transducer array has a uniform shape. In another embodiment, one or more transducer arrays may be shaped differently from the other transducer arrays. Accordingly, the one or more guide portions may be shaped based on the shape of a transducer array intended to be placed according to the guide portion. For example, one of the transducer arrays may be round and a corresponding guide portion may be shaped to accommodate the round transducer array. Another of the transducer arrays may be square and a corresponding guide portion may be shaped to accommodate the square transducer array. transducer arrays may be hexagonal and a corresponding guide portion may be shaped to accommodate the hexagonal transducer array.

In an aspect, engagement/alignment of the one or more landmarks by the one or more engagement portions causes the one or more guide portions to be positioned such that transducer arrays placed according to the guide portions generate a desired electric field strength in a tumor located in the portion of the body.

In an aspect, the physical apparatus may be placed on the portion of the body and the transducer array(s) placed according to the guide portions and affixed to the portion of the body. The physical apparatus may be removed after the transducer arrays are affixed. In another aspect, the one or more transducer arrays may be placed into the guide portions before placement of the physical apparatus onto the portion of the body. The physical apparatus, and placed transducer arrays, may then be placed on the portion of the body, thereby affixing the transducer arrays to the portion of the body. In another aspect, the physical apparatus may remain on the patient while the transducer arrays are in operation. Once a treatment session has concluded, the physical apparatus and the transducer arrays may be removed.

As shown in FIG. 10, FIG. 11A, and FIG. 11B, an apparatus may comprise an engagement portion 1000 for wrapping around a portion of a body of a patient. The apparatus 1000 may comprise one or more guide portions 1002-1008. The one or more guide portions 1002-1008 can comprise a first guide portion 1002, a second guide portion 1008, a third guide portion 1004, and a fourth guide portion 1006. In an embodiment, the apparatus 1000 may comprise only one of the one or more guide portions 1002-1008, such an embodiment is useful in placing TAs on areas of the body the patient cannot readily see either directly or with the help of a mirror. Thus, a patient may utilize multiple apparatuses 1000 to guide the placement of transducer arrays. As shown, the one or more guide portions 1002-1008 may comprise openings in the engagement portion 1000 sized and positioned to guide placement of one or more transducer arrays.

The first guide portion 1002 may be located on the opposite side of the apparatus from the second guide portion 1008. The third guide portion 1004 may be located on the opposite side of the apparatus from the fourth guide portion 1006. The first guide portion 1002 and the second guide portion 1008 may be configured (e.g., shaped, positioned, etc.) for guiding placement of a first pair of transducer arrays. The third guide portion 1004 and the fourth guide portion 1006 may be configured (e.g., shaped, positioned, etc.) for guiding placement of a second pair of transducer arrays. The apparatus may be worn during treatment or may comprise one or more attachment points that enable the apparatus to be removed after placement of the transducer arrays, before treatment.

FIG. 12 shows an apparatus 1200 for guiding placement of a single transducer array. comprising an engagement portion 1202 that is configured (e.g., shaped, positioned, etc.) for engaging a forehead of a patient, an engagement portion 1204 configured (e.g., shaped, positioned, etc.) for engaging a top of a head of the patient, and an engagement portion 1206 configured (e.g., shaped, positioned, etc.) for engaging a side of a head of the patient. The apparatus 1200 comprises a first guide portion 1208 and a second guide portion 1210. The first guide portion 1208 is positioned to guide the placement of a top of a transducer array and the second guide portion 1210 is positioned to guide placement of a side of the transducer array. The apparatus may be worn during treatment or may comprise one or more attachment points that enable the apparatus to be removed after placement of the transducer arrays, before treatment.

The apparatus may be generated via 3D printing or any suitable manufacturing method. The patient model may comprise a surface that corresponds to a location at which one or more transducer arrays are to contact the portion of the body. The surface data and the position data may be derived/obtained from the three-dimensional array layout map and used by the apparatus modeling application 612 to generate a 3D apparatus model. The 3D apparatus model may be stored in digital form, such as a 3D printable file format (e.g., .STL, .OBJ, .FBX, COLLADA, .3DS, .IGES, .STEP, .gcode, .VRML, .3MF, .X3G, etc.).

In some embodiments, a surface of the portion of the body may be identified automatically. For example, the apparatus modeling application 612 may compute various dimensions and/or analyze the curvature of the patient model and deduce one or more surfaces that correspond to a position for one or more transducer arrays and one or more landmarks suitable for engaging an apparatus. In some implementations, a clinician or technician may directly specify the surface. Such implementations may allow for a whole or partial change of a previously generated surface (e.g., as generated by the apparatus modeling application 612) and may impute some therapeutic benefit (e.g., increased or decreased pressure on a particular area of the body part, for example, an area of skin irritation). In one embodiment, various algorithms may be used to determine the optimal shapes and mechanical properties of the apparatus, which are described by the 3D apparatus model. The 3D apparatus model may include information such as, but not limited to, lattice designs and layouts, mesh perforation properties (e.g., hole size/shapes, pitch, etc.), curve locations, variations in lattice density, variable thicknesses, etc. Once the surface is identified, an extrusion operation may be performed on the surface, resulting in the 3D apparatus model.

In an embodiment, the apparatus modeling application 612 generates one or more surfaces that may be form top, bottom, interior, exterior, etc., surfaces of a solid or hollow model of the apparatus, as described by the 3D apparatus model. In an aspect, the one or more surfaces may be combined and/or coupled together. Also, lattice and mesh structures can be generated to define the shape of the apparatus. As illustrated in FIG. 13A, a 3D apparatus model 1300 is depicted, including an engagement portion 1302 and a guide portion 1304. The engagement portion 1302 may be configured to fit under a patient's arm with the engagement portion 1302 engaging an armpit of the patient. The guide portion 1304 may comprise a curved portion marking which should be aligned with a top of a transducer array.

Once produced based on the 3D apparatus model, the apparatus will have a patient-registered surface and a non-patient-registered surface. The patient-registered surface comprises a surface that is in contact with the portion of the body. The non-patient-registered surface comprises a surface that is not in contact with the portion of the body. The non-patient-registered surface may be modified in any suitable manner, for example, to include additional structural features (e.g., buckles for coupling to other components, adhesives, patient/clinician/manufacturer identifying information, etc.).

The 3D apparatus model may be transmitted to a 3D printer. The 3D may produce the apparatus based on the 3D apparatus model. In one implementation, the 3D apparatus model is in a suitable format for 3D printing. In one implementation, the 3D apparatus model is converted into a suitable format for 3D printing before transmitting the 3D apparatus model to the 3D printer. In one implementation, the 3D apparatus model may define one or more layers within the apparatus. The layers may then be printed and laminated together. In one implementation, the 3D apparatus model may describe one or more portions that form an inverse representation (e.g., a mold cavity) of the apparatus, and the inverse representation may be filled with material including, but not limited to, urethane, epoxy, wax, plastic, metal, or foam. In one implementation, the material of the one or more layers may include, but is not limited to, nylon, antimicrobial nylon, ABS plastic, PLA plastic, polyurethane, leather, foam, or combinations thereof. The printed apparatus may be colored by dyeing or through chemical or photo exposure. The printed apparatus may be covered with a material, such as leather, neoprene, a fabric, etc.

In another embodiment, the apparatus modeling application 612 may generate a 2D representation of the 3D apparatus model. The 2D representation may comprise a two-dimensional construction diagram that, when printed on suitable material such as paper, indicates a pattern. The pattern may be used to fold and/or cut the material into a three-dimensional apparatus for guiding the placement of one or more transducer arrays. The 3D apparatus model may define a set of geometry, such as a mesh of triangles or polygons or a set of non-uniform rational basis spines used to represent the apparatus. The apparatus modeling application 612 may convert or unwrap (e.g., UV mapping) the 3D apparatus model to a 2D file format that is dimensionally proportional to the 3D apparatus model.

The apparatus modeling application 612 may generate a UV overlay guide (e.g., two-dimensional construction diagram) that may be used to visualize how the 2D representation may match up with the 3D apparatus model's surface coordinates. To design and calibrate the UV overlay or map, the 3D apparatus model may be retopologized. When the 3D apparatus model is generated, the patient apparatus modeling application 612 may create a mesh of the 3D apparatus model into a high polygon count mesh that may be too complicated to be unwrapped. Retopologization may adjust the mesh of the 3D apparatus model in a variety of ways including changing from a high polygon count mesh to a low count polygon mesh, usually also changing the individual polygons from triangles to squares or rectangles for easier unwrap. Also, the direction of the polygons in the mesh may be changed through retopologization. Also, retopologization provides the ability to adjust how the apparatus will fit to the portion of the body. Also, during the retopologization process, one or more seams may be specified that represent cutting, sewing, and/or folding lines. The UV overlay guide may be converted into a printable file. The printable file may be transmitted to a printer and used to generate a physical copy of the 2D representation.

Figure 14:
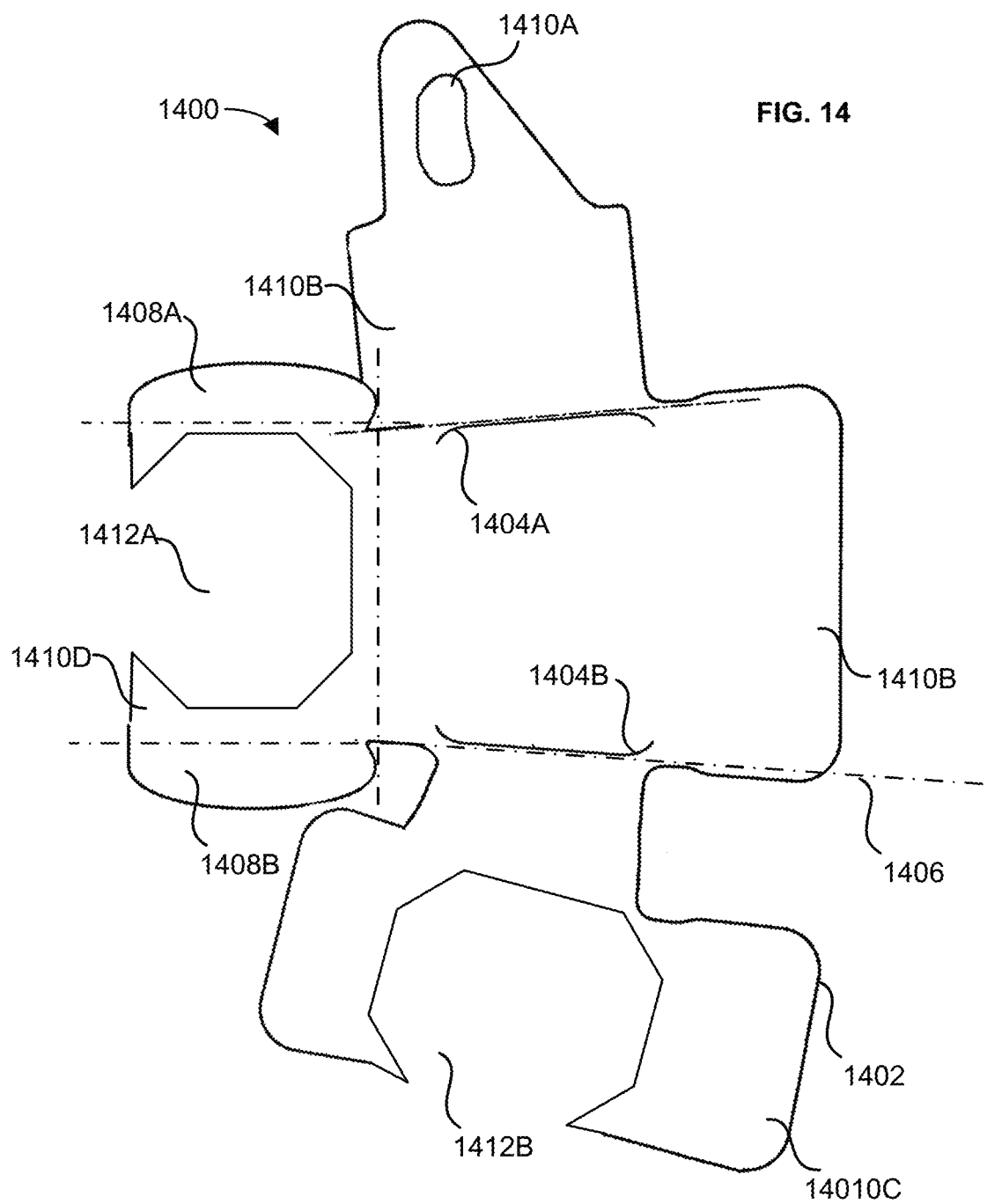
FIG. 14 shows an example of a printed two dimensional construction diagram.

FIG. 14 shows an example of a printed two-dimensional construction diagram that may be cut and/or folded to create an apparatus 1400 for guiding placement of one or more transducer arrays. Solid lines 1402 indicate where the apparatus 1400 may be cut from the material upon which the two-dimensional construction diagram was printed, such as paper, cloth, leather, cardboard, and the like. Solid lines 1404 indicate where a slot may be cut into the material. Dashed and dotted lines 1406 indicate where the material may be folded. Tabs 1408 may be inserted into the slots. For example, tab 1408A may be inserted into slot 1404A, tab 1408B may be inserted into tab 1404A, and tab 1408B may be inserted into slot 1404B. Once folded, cut, and assembled, one or more engagement portions 1410 are created including an engagement portion 1410A (a hole shaped to engage a right ear of a head of a patient), an engagement portion 1410B (a plane configured to engage a top part of the head of the patient), an engagement portion 1410C (a plane configured to engage a left side of the head of the patient), and an engagement portion 1410D (a plane configured to engage a back part of the head of the patient). Additionally, once folded, cut, and assembled, one or more guide portions 1412 are created, including a guide portion 1412A (configured for guiding placement of a transducer array onto the back of the head) and a guide portion 1412C (configured for guiding placement of a transducer array onto the left side of the head).

Figure 15:
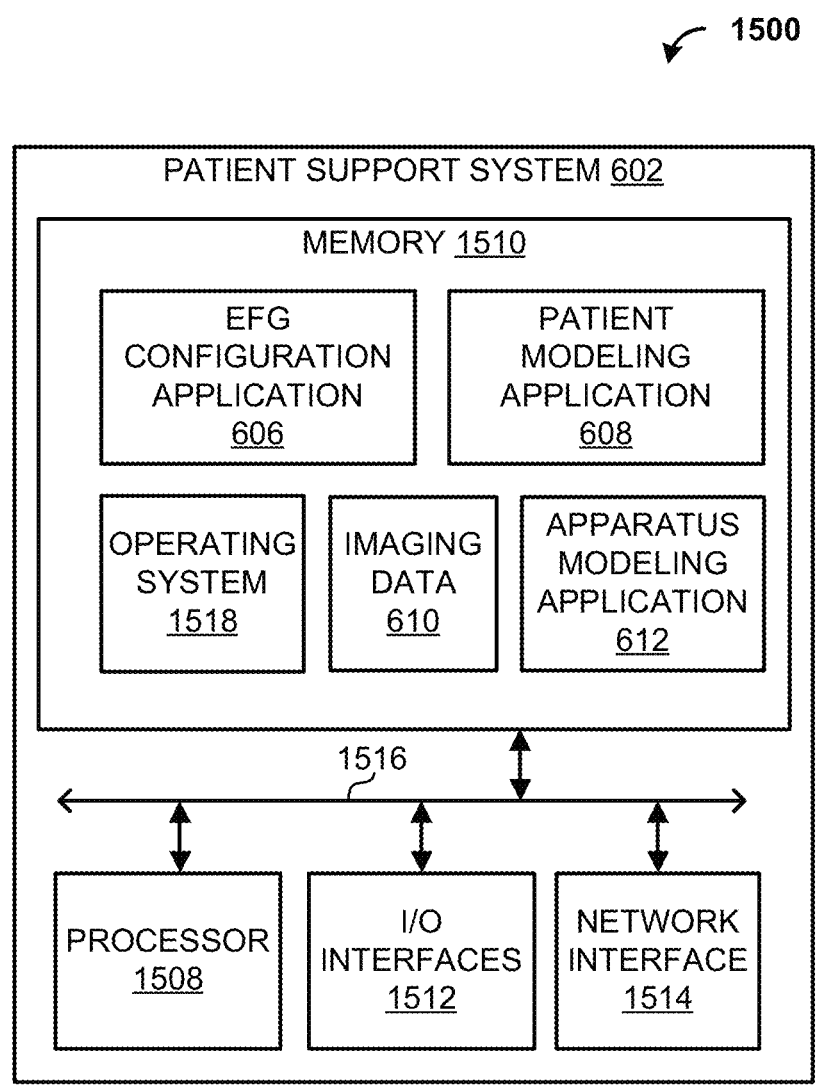
FIG. 15 is a block diagram depicting an example operating environment.

FIG. 15 is a block diagram depicting an environment 1500 comprising a non-limiting example of the patient support system 602. In an aspect, some or all steps of any described method may be performed on a computing device as described herein. The patient support system 602 can comprise one or multiple computers configured to store one or more of the EFG configuration application 606, the patient modeling application 608, the imaging data 610, the apparatus modeling application 612, and the like.

The patient support system 602 can be a digital computer that, in terms of hardware architecture, generally includes a processor 1508, memory system 1510, input/output (I/O) interfaces 1512, and network interfaces 1514. These components (1508, 1510, 1512, and 1514) are communicatively coupled via a local interface 1516. The local interface 1516 can be, for example, but not limited to, one or more buses or other wired or wireless connections, as is known in the art. The local interface 1516 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1508 can be a hardware device for executing software, particularly that stored in the memory system 1510. The processor 1508 can be any custom made or commercially available processor, a central processing unit (CPU), an auxiliary processor among several processors associated with the patient support system 602, a semiconductor-based microprocessor (in the form of a microchip or chipset), or generally any device for executing software instructions. When the patient support system 602 is in operation, the processor 1508 can be configured to execute software stored within the memory system 1510, to communicate data to and from the memory system 1510, and to generally control operations of the patient support system 602 according to the software.

The I/O interfaces 1512 can be used to receive user input from and/or for providing system output to one or more devices or components. User input can be provided via, for example, a keyboard and/or a mouse. System output can be provided via a display device and a printer (not shown). I/O interfaces 1512 can include, for example, a serial port, a parallel port, a Small Computer System Interface (SCSI), an IR interface, an RF interface, and/or a universal serial bus (USB) interface.

The network interface 1514 can be used to transmit and receive from the patient support system 602. The network interface 1514 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1514 may include address, control, and/or data connections to enable appropriate communications.

The memory system 1510 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1510 may incorporate electronic, magnetic, optical, and/or other types of storage media. Note that the memory system 1510 can have a distributed architecture, where various components are situated remote from one another, but can be accessed by the processor 1508.

The software in memory system 1510 may include one or more software programs, each of which comprises an ordered listing of executable instructions for implementing logical functions. In the example of FIG. 15, the software in the memory system 1510 of the patient support system 602 can comprise the EFG configuration application 606, the patient modeling application 608, the imaging data 610, the apparatus modeling application 612, and a suitable operating system (O/S) 1518. The operating system 1518 essentially controls the execution of other computer programs, and provides scheduling, input-output control, file and data management, memory management, and communication control and related services.

For purposes of illustration, application programs and other executable program components such as the operating system 1518 are illustrated herein as discrete blocks, although it is recognized that such programs and components can reside at various times in different storage components of the patient support system 602. An implementation of the EFG configuration application 606, the patient modeling application 608, the imaging data 610, the apparatus modeling application 612, and/or the control software 110 can be stored on or transmitted across some form of computer-readable media. Any of the disclosed methods can be performed by computer readable instructions embodied on computer-readable media. Computer-readable media can be any available media that can be accessed by a computer. By way of example and not meant to be limiting, computer-readable media can comprise "computer storage media" and "communications media." "Computer storage media" can comprise volatile and non-volatile, removable and non-removable media implemented in any methods or technology for storage of information such as computer-readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can b e accessed by a computer.

Figure 16:
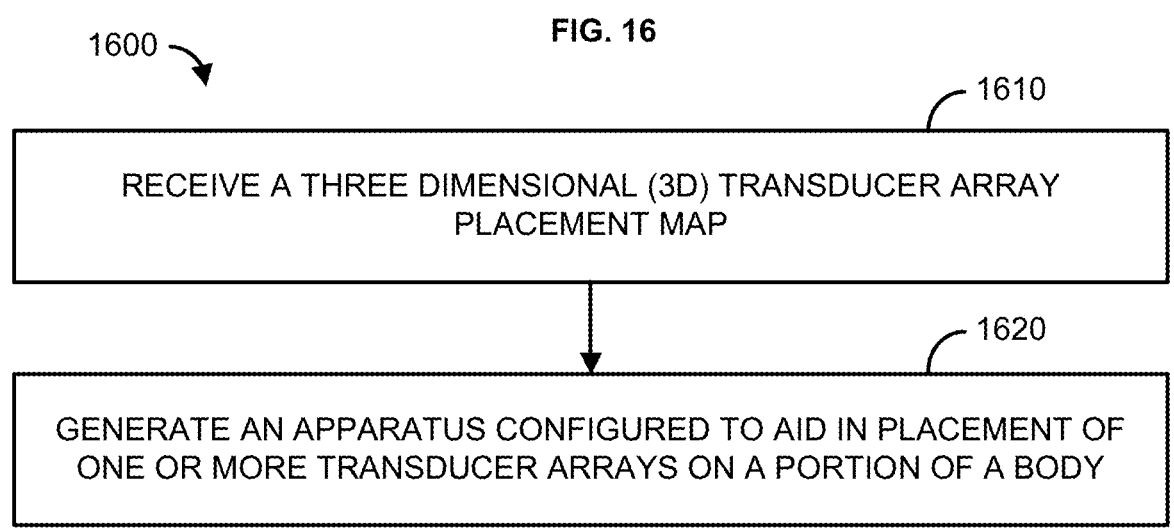
FIG. 16 shows an example method.

In an embodiment, illustrated in FIG. 16, one or more of the patient modeling application 608 and/or the apparatus modeling application 612 can be configured to perform a method 1600 comprising receiving a three dimensional (3D) transducer array placement map at 1610. The method 1600 can comprise generating, based on the 3D transducer array placement map, an apparatus configured to aid in the placement of one or more transducer arrays on a portion of a body at 1620. The portion of the body can comprise a neck, a head, a torso, a pelvis, an abdomen, a leg, an arm, a hand, or a foot. The apparatus can be comprised of leather, cloth, plastic, paper, or metal.

The method 1600 can further comprise receiving imaging data of the portion of the body. The method 1600 can further comprise determining, based on the 3D transducer array placement map, position data associated with the placement of the one or more transducer arrays on the portion of the body, wherein the position data is indicative of placement of the one or more transducer arrays on the portion of the body that results in a desired electric field strength in a tumor within the portion of the body. The method 1600 can further comprise determining, based on the imaging data, surface data associated with the portion of the body, wherein the surface data corresponds to one or more landmarks of the portion of the body. The method 1600 can further comprise determining, based on the surface data and the position data, a 3D model of the apparatus, wherein the 3D model comprises one or more features configured to engage the one or more landmarks and one or more features configured to guide placement of the one or more transducer arrays. Generating the apparatus can comprise causing the apparatus to be printed via a 3D printer according to the 3D model of the apparatus.

The method 1600 can further comprise determining, based on the 3D transducer array placement map, a two-dimensional construction diagram. Generating the apparatus can comprise printing the two-dimensional construction diagram on paper.

In view of the described apparatuses, systems, and methods and variations thereof, herein below are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1: A method comprising receiving a three dimensional (3D) transducer array placement map and generating, based on the 3D transducer array placement map, an apparatus configured to aid in placement of one or more transducer arrays on a portion of a body.

Embodiment 2: The embodiment as in any one of the preceding embodiments, further comprising determining, based on the 3D transducer array placement map, position data associated with placement of the one or more transducer arrays on the portion of the body, wherein the position data is indicative of placement of the one or more transducer arrays on the portion of the body that results in a desired electric field strength in a tumor within the portion of the body.

Embodiment 3: The embodiment as in any one of the preceding embodiments, further comprising receiving imaging data of the portion of the body.

Embodiment 4: The embodiment as in any one of the preceding embodiments, further comprising determining, based on the imaging data, surface data associated with the portion of the body, wherein the surface data corresponds to one or more landmarks of the portion of the body.

Embodiment 5: The embodiment as in any one of the preceding embodiments further comprising determining, based on the surface data and the position data, a 3D model of the apparatus, wherein the 3D model comprises one or more features configured to engage the one or more landmarks and one or more features configured to guide placement of the one or more transducer arrays.

Embodiment 6: The embodiment as in any one of the preceding embodiments wherein generating the apparatus comprises causing the apparatus to be printed via a 3D printer according to the 3D model of the apparatus.

Embodiment 7: The embodiment as in any one of the preceding embodiments further comprising determining, based on the 3D transducer array placement map, a two dimensional construction diagram.

Embodiment 8: The embodiment as in any one of the preceding embodiments wherein generating the apparatus comprises printing the two dimensional construction diagram on paper.

Embodiment 9: The embodiment as in any one of the preceding embodiments wherein the portion of the body comprises a neck, a head, a torso, a pelvis, an abdomen, a leg, an arm, a hand, or a foot.

Embodiment 10: The embodiment as in any one of the preceding embodiments, wherein the apparatus is comprised of leather, cloth, plastic, paper, or metal.

Embodiment 11: An apparatus comprising: a shell, contoured to fit a portion of a body, wherein the shell comprises, one or more engagement portions configured to engage one or more landmarks of the portion of the body, and one or more guide portions, wherein each of the one or more guide portions is configured to guide placement of the one or more transducer arrays, wherein engagement of the one or more landmarks by the one or more engagement portions causes the one or more guide portions to be positioned such that transducer arrays placed according to the guide portions generate a desired electric field strength in a tumor located in the portion of the body.

Embodiment 12: The embodiment as in any one of embodiments 11-20 wherein the one or more engagement portions comprise one or more of a strap, a buckle, a slot, hole, or an adhesive.

Embodiment 13: The embodiment as in any one of embodiments 11-20 wherein the one or more guide portions are indicative of a position for each transducer array to generate an electric field having a desired strength in a tumor located in the portion of the body.

Embodiment 14: The embodiment as in any one of embodiments 11-20 wherein the one or more guide portions comprises a first guide portion, a second guide portion, a third guide portion, and a fourth guide portion.

Embodiment 15: The embodiment as in any one of embodiments 11-20 wherein the first guide portion is located on an opposite side of the shell from the second guide portion.

Embodiment 16: The embodiment as in any one of embodiments 11-20 wherein the third guide portion is located on an opposite side of the shell from the fourth guide portion.

Embodiment 17: The embodiment as in any one of embodiments 11-20 wherein the first guide portion and the second guide portion are configured for guiding placement of a first pair of transducer arrays.

Embodiment 18: The embodiment as in any one of embodiments 11-20 wherein the third guide portion and the fourth guide portion are configured for guiding placement of a second pair of transducer arrays.

Embodiment 19: The embodiment as in any one of embodiments 11-20 wherein the portion of the body comprises a neck, a head, a torso, a pelvis, an abdomen, a leg, an arm, a hand, or a foot.

Embodiment 20: The embodiment as in any one of embodiments 11-20 wherein the shell is comprised of leather, cloth, plastic, paper, or metal.

Embodiment 21: A method comprising receiving a three dimensional (3D) model of an apparatus configured to aid in placement of one or more transducer arrays on a portion of a body and generating, based on the 3D model of the apparatus, the apparatus.

Embodiment 22: The embodiment as in any one of embodiments 21-30 further comprising determining, based on a 3D transducer array placement map, position data associated with placement of the one or more transducer arrays on the portion of the body, wherein the position data is indicative of placement of the one or more transducer arrays on the portion of the body that results in a desired electric field strength in a tumor within the portion of the body.

Embodiment 23: The embodiment as in any one of embodiments 21-30 further comprising receiving imaging data of the portion of the body.

Embodiment 24: The embodiment as in any one of embodiments 21-30 further comprising determining, based on the imaging data, surface data associated with the portion of the body, wherein the surface data corresponds to one or more landmarks of the portion of the body.

Embodiment 25: The embodiment as in any one of embodiments 21-30 further comprising determining, based on the surface data and the position data, the 3D model of the apparatus, wherein the 3D model comprises one or more features configured to engage the one or more landmarks and one or more features configured to guide placement of the one or more transducer arrays.

Embodiment 26: The embodiment as in any one of embodiments 21-30 wherein generating the apparatus comprises causing the apparatus to be printed via a 3D printer according to the 3D model of the apparatus.

Embodiment 27: The embodiment as in any one of embodiments 21-30 further comprising determining, based on the 3D transducer array placement map, a two dimensional construction diagram.

Embodiment 28: The embodiment as in any one of embodiments 21-30 wherein generating the apparatus comprises printing the two dimensional construction diagram on paper.

Embodiment 29: The embodiment as in any one of embodiments 21-30 wherein the portion of the body comprises a neck, a head, a torso, a pelvis, an abdomen, a leg, an arm, a hand, or a foot.

Embodiment 30: The embodiment as in any one of embodiments 21-30 wherein the apparatus is comprised of leather, cloth, plastic, paper, or metal.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
receiving a three dimensional (3D) transducer array placement map; and
generating, based on the 3D transducer array placement map, an apparatus configured to aid in placement of one or more transducer arrays on a portion of a body.

2. The method of claim 1, further comprising determining, based on the 3D transducer array placement map, position data associated with placement of the one or more transducer arrays on the portion of the body, wherein the position data is indicative of placement of the one or more transducer arrays on the portion of the body that results in a desired electric field strength in a tumor within the portion of the body.

3. The method of claim 1, further comprising:
receiving imaging data of the portion of the body; and
determining, based on the imaging data, surface data associated with the portion of the body, wherein the surface data corresponds to one or more landmarks of the portion of the body.

4. The method of claim 3, further comprising determining, based on the surface data and the position data, a 3D model of the apparatus, wherein the 3D model comprises one or more features configured to engage the one or more landmarks and one or more features configured to guide placement of the one or more transducer arrays.

5. The method of claim 4, wherein generating the apparatus comprises causing the apparatus to be printed via a 3D printer according to the 3D model of the apparatus.

6. The method of claim 1, further comprising determining, based on the 3D transducer array placement map, a two-dimensional construction diagram.

7. The method of claim 6, wherein generating the apparatus comprises printing the two-dimensional construction diagram on paper.

8. The method of claim 1, wherein the apparatus is comprised of leather, cloth, plastic, paper, or metal.

9. An apparatus comprising:
a shell, contoured to fit a portion of a body, wherein the shell comprises,
one or more engagement portions configured to engage one or more landmarks of the portion of the body, and
one or more guide portions, wherein each of the one or more guide portions is configured to guide placement of the one or more transducer arrays,
wherein engagement of the one or more landmarks by the one or more engagement portions causes the one or more guide portions to be positioned such that transducer arrays placed according to the guide portions generate a desired electric field strength in a tumor located in the portion of the body.

10. The apparatus of claim 9, wherein the one or more engagement portions comprise one or more of a strap, a buckle, a slot, hole, or an adhesive.

11. The apparatus of claim 9, wherein the one or more guide portions are indicative of a position for each transducer array to generate an electric field having a desired strength in a tumor located in the portion of the body.

12. The apparatus of claim 9, wherein the one or more guide portions comprises a first guide portion, a second guide portion, a third guide portion, and a fourth guide portion.

13. The apparatus of claim 12, wherein at least one of: the first guide portion is located on an opposite side of the shell from the second guide portion, and the third guide portion is located on an opposite side of the shell from the fourth guide portion.

14. The apparatus of claim 12, wherein the first guide portion and the second guide portion are configured for guiding placement of a first pair of transducer arrays.

15. The apparatus of claim 12, wherein the third guide portion and the fourth guide portion are configured for guiding placement of a second pair of transducer arrays.

16. A method comprising:
receiving a three dimensional (3D) model of an apparatus configured to aid in placement of one or more transducer arrays on a portion of a body; and
generating, based on the 3D model of the apparatus, the apparatus.

17. The method of claim 16, further comprising determining, based on a 3D transducer array placement map, position data associated with placement of the one or more transducer arrays on the portion of the body, wherein the position data is indicative of placement of the one or more transducer arrays on the portion of the body that results in a desired electric field strength in a tumor within the portion of the body.

18. The method of claim 16, further comprising:
receiving imaging data of the portion of the body; and
determining, based on the imaging data, surface data associated with the portion of the body, wherein the surface data corresponds to one or more landmarks of the portion of the body.

19. The method of claim 18, further comprising determining, based on the surface data and the position data, the 3D model of the apparatus, wherein the 3D model comprises one or more features configured to engage the one or more landmarks and one or more features configured to guide placement of the one or more transducer arrays.

20. The method of claim 16, wherein generating the apparatus comprises causing the apparatus to be printed via a 3D printer according to the 3D model of the apparatus.

* * * * *